US008283308B2

(12) United States Patent
Mason et al.

(10) Patent No.: US 8,283,308 B2
(45) Date of Patent: Oct. 9, 2012

(54) COPOLYMER-STABILIZED EMULSIONS

(75) Inventors: Thomas G. Mason, Los Angeles, CA (US); Timothy J. Deming, Los Angeles, CA (US); Jarrod A. Hanson, Los Angeles, CA (US); Connie B. Chang, Los Angeles, CA (US); Sara M. Graves, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 567 days.

(21) Appl. No.: 12/391,914

(22) Filed: Feb. 24, 2009

(65) Prior Publication Data
US 2009/0208548 A1 Aug. 20, 2009

Related U.S. Application Data

(63) Continuation of application No. PCT/US2008/009882, filed on Aug. 20, 2008.

(60) Provisional application No. 60/935,605, filed on Aug. 21, 2007.

(51) Int. Cl.
*A61K 38/02* (2006.01)

(52) U.S. Cl. .......................................................... 514/1.1

(58) Field of Classification Search .................. None
See application file for complete search history.

(56) References Cited

U.S. PATENT DOCUMENTS

| 5,820,850 | A | 10/1998 | Hashimoto et al. | |
|---|---|---|---|---|
| 5,922,357 | A | 7/1999 | Coombes et al. | |
| 6,995,209 | B2 * | 2/2006 | Olivieri et al. | 524/801 |
| 2004/0010060 | A1 * | 1/2004 | Joanicot et al. | 523/201 |
| 2006/0254933 | A1 | 11/2006 | Adachi et al. | |
| 2008/0166380 | A1 | 7/2008 | Yamamoto et al. | |

FOREIGN PATENT DOCUMENTS

| JP | 6-505192 | 6/1994 |
|---|---|---|
| WO | WO-92/14781 | 9/1992 |
| WO | WO-2006/057429 A1 | 1/2006 |
| WO | WO 2006/096571 | 1/2006 |

OTHER PUBLICATIONS

Riess et al. Macromolecular Rapid Communications (2004, 25, 401-43).*
International Search Report for PCT/US2008/09882 (Nov. 9, 2008) (2 pgs).
Written Opinion for PCT/US2008/09882 (Nov. 9, 2008) (7 pgs).
J. Bibette, F. Leal-Calderon, and P. Poulin, Rep. Prog. Phys. 62, 969 (1999).
A.S. Utada et al., Science 308, 537 (2005).
C. Goubault et al., Langmuir 17, 5184 (2001).
T. G. Mason, and J. Bibette, Phys. Rev. Lett. 77, 3481 (Oct. 1996).
T. G. Mason, and J. Bibette, Langmuir 13, 4600 (1997).
G. A. Silva et al., Science 303, 1352 (2004).
D. E. Discher, and A. Eisenburg, Science 297, 967 (2002).
D. J. Pochan et al., Macromolecules 35, 5358 (2002).
J. Rodriguez-Hernandez, and S. Lecommandoux, J Am Chem Soc 127, 2026 (2005).
I. W. Hamley, Soft Matter 1, 36 (2005).
A. J. Link, M. L. Mock, and D. A. Tirrell, Curr Opin Biotech 14, 603 (2003).
E. P. Holowaka, D. J. Pochan, and T. J. Deming, J Am Chem Soc 127, 12423 (2005).
E. P. Holowka et al., Nat Mater 6, 52 (Jan. 2007).
Pays, K. et al. Double emulsions: how does release occur? *Journal of Controlled Release* 79, 193-205 (2002).
Davis, S. S. & Walker, I. M. Multiple Emulsions as Targetable Delivery Systems. *Methods in Enzymology* 149, 51-64(1987).
Okuchi, H. & Nakano, M. "Preparation and evaluation of W/O/W type emulsions containing vancomycin", *Advanced Drug Delivery Reviews* 45, 5-26 (2000).
Garti, N. Double emulsions—Scope, limitations and new achievements. Colloids and Surfaces A-Physiochemical and Engineering Aspects 123, 233-246 (1997).
Loscertales, I. G. et al. Micro/nano encapsutation via electrified coaxial liquid jets. Science 295, 1695-1698 (2002).
Utada, A. S. et al. Monodisperse double emulsions generated from a microcapillary device, Science 308, 537-541 (2005).
Morias, J. M., Santos, O. D. H., Nunes, J. R. L., Zanatta, C.F., Rocha-Filho, P.A. W/O/W Multiple emulsions obtained by one-step emulsification method and evaluacation of the involved variables. *Journal of Dispersion Science and Technology* 29, 63-69 (2008).
Mason, T. G., Wilking, J. N., Meleson, K., Chang, C. B. & Graves, S. M. Nanoemulsions: formation, structure, and physical properties. *Journal of Physics-Condensed Matter* 18, R635-R666 (Sep. 2006).
Ficheux, M. F. Bonakdar, L., Leal-Calderon, F. & Bibette, J. Some stability criteria for double emulsions. *Langmuir* 14, 2702-2706 (Apr. 21, 1998).
Yafei, W., Tao, Z. & Gang, H. Structural evolution of polymer-stabilized double emulsions. *Langmuir* 22, 67-73 (2006) Nov. 12, 2005.
Coubault, C. et al. Shear rupturing of complex fluids: Applications to the preparation of quasi-monodisperse water-in-oil-in-water double emulsions. *Langmuir* 17, 5184-5188 (2001).
Okushima, S., Nisisako, T., Torii, T. & Higuchi, T. Controlled production of monodisperse double emulsions by two-step droplet breakup in microfluidic devices. *Langmuir* 20, 9905-9908 (2004).
Benichou, A., Aserin, A., Garti, N. Double emulsions stabilized with hybrids of natural polymers for entrapment and slow release of active matters. *Advances in Colloid and Interface Science* 108-109, 29-41 (2004).

(Continued)

*Primary Examiner* — Johann Richter
*Assistant Examiner* — Jessica Kassa
(74) *Attorney, Agent, or Firm* — Venable LLP; Henry J. Daley

(57) ABSTRACT

An emulsion includes a substantially continuous liquid medium, and a plurality of droplet structures dispersed within the substantially continuous liquid medium. Each droplet structure of the plurality of droplet structures includes an outer droplet of a first liquid having an outer surface; an inner droplet of a second liquid having an inner surface contained within the outer surface of the outer droplet of the first liquid, the second liquid being immiscible in the first liquid, wherein the inner and outer droplets have a boundary surface region therebetween; an outer layer of block copolymers disposed on the outer surface of the outer droplet; and an inner layer of block copolymers disposed on the inner surface of the inner droplet. The block copolymers include a hydrophilic polymer block and a hydrophobic polymer block that act in combination to stabilize the droplet structure, and the first liquid is immiscible in the substantially continuous liquid medium.

50 Claims, 10 Drawing Sheets

OTHER PUBLICATIONS

T. J. Deming, Macromolecules 32, 4500 (1999).

H. F. Klein, and H. H. Karsch, Chem. Ber. 108, 944 (1975).

V. Breedveld et al., Macromolecules 37, 3943 (2004).

Niederhafner, P., Sebestik, J. & Jezek, J. Peptide dendrimers. *Journal of Peptide Science* 11, 757-788 (2005).

Nowak, A. P. et al. Rapidly recovering hydrogel scaffolds from self-assembling diblock copolypeptide amphiphiles. *Nature* 417, 424-428 (2002).

Kricheldord, H. R. & Mang, T. C-13-NMR Sequence-Analysis, 20. Stereospecificity of the Polymerization of D, L-Leu-NCA and D,L-Val-NCA. *Makromolekulare Chemie-Macromolecular Chemistry and Physics* 182, 3077-3098 (1981).

Breitenbach, J. W., Allinger, K. & Koref, A. Viskositatsstudien an Losungen von DL-Phenylalanin-Polypeptiden. *Monatsh. Chem* 86, 269 (1955).

Lapp, C. & Marchal, J. Preparation De la Poly-D,L-Phenylalanine En Helice Par Polymerisation De La D,L-Benzyl-4 Oxazolidine Dione-2-5. *Journal De Chemie Physique Et De Physico-Chimie Biologique* 60, 756-766 (1963).

Kataoka, K., Kwon, G. S., Yokoyama, M., Okano, T. & Sakurai, Y. Block-Copolymer Micelles as Vehicles for Drug Delivery. *Journal of Controlled Release* 24, 119-132 (1993).

Strey, R. Microemulsion Microstructure and interfacial curvature. Colloid and Polymer Science 272, 1005-1019 (1994).

Enser, M., Bloomberg, G. B., Brock, C., Clark, D.C. De novo design and structure activity relationships of peptide emulsifiers and foaming agents. *International Journal of Biological Macromolecules* 12, 118-124 (1990).

Dickinson, E. Structure and composition of adsorbed protein layers and the relationship to emulsion stability. *Journal of the Chemical Society Faraday Transactions* 88, 2973-2983 (1992).

Saito, M., Ogasawara, M., Chikuni, K., Shimizu, M. Synthesis of a peptide emulsifier with an amphiphilic structure. *Bioscience, Biotechnology and Biochemistry* 59, 388-392 (1995).

Dalgleish, D. G. Conformations and structures of milk proteins adsorbed to oil-water interfaces. *Food Research International* 29, 541-547 (1996).

Chang, C. B., Knobler, C. M., Gelbart, W. M., Mason, T. G. Curvature Dependency of Viral Protein Structures on Encapsidated Nenoemulsion Droplets. ACS Nano 2, 281-286 (Feb. 2, 2008).

\* cited by examiner

COPOLYMER-STABILIZED EMULSIONS

CROSS-REFERENCE TO RELATED APPLICATION

This application is a continuation of International Application No. PCT/US2008/009882, filed Aug. 20, 2008, and claims priority to U.S. Provisional Application No. 60/935,605, filed Aug. 21, 2007 the entire contents of each of which are hereby incorporated by reference.

This invention was made using U.S. Government support under Grant No. CHE-0415275, awarded by the National Science Foundation. The U.S. Government has certain rights in this invention.

BACKGROUND

1. Field of Invention

The present invention relates to droplet structures, emulsions of droplet structures and methods of producing the droplet structures and emulsions; and more particularly to droplet structures, emulsions of droplet structures and methods of producing the droplet structures that are stabilized with block copolymers.

2. Discussion of Related Art

Simple emulsions are dispersions of droplets of one liquid in another immiscible liquid; the droplets are typically formed by applied shear and stabilized against subsequent coalescence by a surfactant that provides an interfacial repulsion (J. Bibette, F. Leal-Calderon, and P. Poulin, Rep. Prog. Phys. 62, 969 (1999)). (All references cited anywhere in any section of this specification are incorporated herein by reference.) Two of the most common types are 'direct' oil-in-water (O/W) emulsions and 'inverse' water-in-oil (W/O) emulsions. Surfactants are amphiphilic molecules that can take many different forms: ionic (e.g. anionic, cationic, zwitterionic), non-ionic (e.g. ethoxylated alkane chains), and polymeric (e.g. simple, diblock, and triblock polymers). Because they are amphiphilic, surfactants tend to preferentially adsorb onto oil-water interfaces. The relative solubility of the surfactant in the oil and the water, the concentration of the surfactant, and the degree of interfacial repulsion that the surfactant provides once it has adsorbed onto the interfaces are important factors in determining the stability and longevity of emulsions that are formed by an applied shear flow or other sources of non-thermal external stresses that can cause bigger droplet structures to be ruptured into smaller droplet structures.

Beyond simple emulsions, higher levels of topological complexity exist. For instance, a W/O emulsion can be sheared into an aqueous continuous liquid, thereby creating a dispersion of oil droplets which themselves contain smaller water droplets. Through judicious choice of the surfactants, both the 'inner' water droplets inside the oil droplets, as well as the larger oil droplets themselves, can remain stable over long periods of time. This type of emulsion is called a water-in-oil-in-water (W/O/W) emulsion. Emulsion systems that have this level of topological complexity are generically called 'double emulsions' because, starting from the continuous liquid phase, two oil-water interfacial layers must be penetrated to reach the center of the smallest droplet structure. Indeed, through successive controlled emulsification steps, it is possible to fabricate triple emulsions and even higher topologically ordered multiple emulsions that contain many interfacial layers that must be penetrated in order to reach the center of the smallest droplet structure in the system. A W/O/W double emulsion may have outer oil droplets that each contain only one inner water droplet. However, it is also possible for oil droplets in a W/O/W double emulsion to contain many inner water droplets. Sometimes, this is mistakenly referred to as a "multiple emulsion". Instead, more properly, it should be referred to as a W/O/W double emulsion that has outer oil droplets that generally each contain a plurality of multiple inner droplets. Two average droplet volume fractions can be used to characterize a double emulsion roughly: the average 'inner volume fraction' of water droplets inside the oil droplets, and the average 'outer volume fraction' of the W/O droplets that exist in the continuous aqueous solution. Generally, there is a full distribution of radii corresponding to inner water droplets and also a different distribution of radii corresponding to outer water droplets. It can be desirable for these distributions to exhibit monomodal peaks that are fairly sharp, so the droplet sizes are more highly controlled, or 'uniform'. Another structural aspect that characterizes double emulsions is the probability distribution of the number of inner droplets per outer droplet. Although we focus primarily on creating W/O/W double emulsions (i.e. water-borne double droplets) herein, it is equally possible to create oil-in-water-in-oil (O/W/O) double emulsions that do not have an aqueous continuous phase. For oil-in-water single emulsions and for water-in-oil-in-water double emulsions, $\phi$ is typically used to designate the oil volume fraction: the volume of oil contained within the emulsion system divided by the total volume of the emulsion system.

In recent years, two primary pathways, structured microfluidic and sequential emulsification, have provided highly uniform W/O/W double emulsions that typically have average outer droplet diameters greater than about one micron. The first pathway is through relatively low-throughput microfluidic methods. In one implementation of this pathway, a W/O/W emulsion is created using a first cross-channel flow junction to produce water droplets in oil and then using a second cross-channel flow junction to rupture the W/O droplets into a continuous aqueous phase (S. Okushima et al., Langmuir 20, 9905 (2004)). Alternatively, porous glass emulsification and membrane emulsification methods, rather than micromachined fluidic channels, can be used to provide highly uniform W/O emulsions at higher throughput. This implementation permits quite robust incorporation of many inner droplets into double emulsions. A second implementation of microfluidic rupturing is by structuring the flow of an innermost water jet, an intermediate oil jet, and an outermost water jet using microfluidic channels, such that the capillary instability of the inner and outer interfaces occurs simultaneously (A. S. Utada et al., Science 308, 537 (2005)). This method is good for encapsulating objects in the innermost aqueous jet into a W/O/W double emulsion containing a single inner droplet. However, it is significantly more difficult to coordinate the flows so that double emulsions containing a specific number of multiple inner droplets are formed at the desired internal volume fraction. In both of these microfluidic approaches, appropriate surfactants must be present in the liquid phases in order to preserve the stability of the emulsion after formation.

The second pathway is the more traditional form of sequential emulsification without the use of micromachined channels. In sequential emulsification, a W/O emulsion is first created, and then this simple inverse emulsion is, in turn, emulsified into an aqueous surfactant solution using shear (W. Yafei, Z. Tao, and H. Gang, Langmuir 22, 67 (2006)). If desired, both the water and the oil droplets in this W/O/W double emulsion can be size-fractionated to make them monodisperse. Without fractionation, the traditional method can be very high-throughput and can produce many liters per hour. If a high level of monodispersity is desired, then the fractionation necessarily slows down the process. In a variation on this method, a high-throughput approach for making the oil droplets quasi-monodisperse by shearing a premixed double emulsion in a thin gap (C. Goubault et al., Langmuir 17, 5184 (2001)) uses a method previously developed for making monodisperse simple emulsions (T. G. Mason, and J. Bibette, Phys. Rev. Lett. 77, 3481 (1996); T. G. Mason, and J. Bibette, Langmuir 13, 4600 (1997)). As for double emulsions produced using microfluidic methods, the choice of surfactants for sequential emulsification is also important in order to obtain the desired properties of stability and release.

Similar to small molecule surfactants and lipids, synthetic block copolymers are able to self-assemble into ordered nanostructures via microphase separation of the polymeric components (A. J. Link, M. L. Mock, and D. A. Tirrell, Curr Opin Biotech 14, 603 (2003)). However, the ability of block copolymers to assemble into hierarchically structured materials or distinct tertiary structures, similar to those found in biological systems (e.g. proteins), has been limited by the random coiled nature of most common polymers as well as the limited functionality of the polymer domains. Incorporation of elements that encourage hydrogen-bonding (G. A. Silva et al., Science 303, 1352 (2004)), amphiphilicity (D. E. Discher, and A. Eisenberg, Science 297, 967 (2002)), crystallization (G. D. Fasman, *Prediction of protein structure and the principles of protein conformation* (Plenum Press, New York, 1989), pp. xiii), and liquid crystal formation (D. J. Pochan et al., Macromolecules 35, 5358 (2002)) would all serve to influence structural evolution (J. Rodriguez-Hernandez, and S. Lecommandoux, J Am Chem Soc 127, 2026 (2005)). Increasing the complexity of copolymer sequences (di- to tri- to tetra-blocks, etc.) would also enhance the potential for hierarchical assembly (I. W. Hamley, Soft Matter 1, 36 (2005)). The main limitation in utilizing these strategies is that the synthetic chemistry necessary for preparation of functional, multicomponent block copolymers is a major hindrance due to incompatibilities of different monomers with a given polymerization method (A. J. Link, M. L. Mock, and D. A. Tirrel, Curr Opin Biotech 14, 603 (2003)). Furthermore, since most common synthetic polymers lack the intricate complexity found in biopolymers (e.g. secondary structure, complex functionality and stereochemistry), they may never be able to faithfully mimic the behavior of sell-assemble biological macromolecules. For these reasons, prior to investigating emulsion systems, we have studied the self-assembly of block copolypeptides as synthetic materials that possess the ability to aggregate into specifically defined, functional nanostructures, including vesicles and hydrogels. These non-emulsion materials typically form through interactions between the copolypeptide molecules resulting in "bottom-up" self-assembly. However, the use of synthetic constituents (i.e. non-amino acid monomers) to form synthetic polymer blocks and the use of higher tri-block and multi-block polymer structures are not excluded from some of the general concepts of the current invention.

In work preceding the invention described herein, we focused our efforts on studying the roles of chain length and block composition on the assembly of small, charged diblock copolypeptide amphiphiles, where we utilized the structure directing properties of a rod-like α-helical segment in the hydrophobic domain. Specifically, we prepared and studied the aqueous self-assembly of a series of poly(L-lysine)-b-poly(L-leucine) block copolypeptides, $K_xL_y$, where x ranged from 20 to 80, and y ranged from 10 to 30 residues, as well as the poly(L-glutamatic acid)-b-poly(L-leucine) block copolypeptide, $E_{60}L_{20}$ (E. P. Holowka, D. J. Pochan, and T. J. Deming, J Am Chem Soc 127, 12423 (2005)). The poly(L-lysine.HBr) and poly(L-glutamate-$Na^+$) segments are highly charged polyelectrolytes at neutral pH and dissolve readily in water. In earlier work, we found that samples with high K to L molar ratios (e.g. $K_{180}L_{20}$) could be dissolved directly into deionized water, yielding transparent hydrogels composed of twisted fibrils (A. P. Nowak et al., Nature 417, 424 (2002)). We reasoned that use of shortened charged segments would relax repulsive polyelectrolyte interactions and allow formation of charged polypeptide membranes. In our first series of copolymers, the size of the oligoleucine domain was held constant at 20 residues, and the oligolysine domain was varied from 20 to 80 residues. Samples were processed by suspending dry polymer in THF/water (1:1) followed by dialysis. Analysis of these assemblies using DIC optical microscopy revealed the presence of large, sheet-like membranes for $K_{20}L_{20}$, and thin fibrils for $K_{40}L_{20}$. The $K_{60}L_{20}$ sample was most promising, as only large vesicular assemblies were observed by differential interference contrast (DIC) microscopy (E. P. Holowka, D. J. Pochan, and T. J. Deming, J Am Chem Soc 127, 12423 (2005)).

The $K_{60}L_{20}$ polypeptide vesicles obtained directly from dialysis are polydisperse and range in diameter from ca. 5 μm down to 0.8 μm as determined using DIC and DLS (FIG. 1). For applications such as drug delivery via blood circulation, a vesicle diameter of ca. 50 nm to about 100 nm, even up to about 200 nm, is desired. We found that aqueous suspensions of $K_{60}L_{20}$ vesicles could be extruded through nuclear track-etched polycarbonate (PC) membranes with little loss of polypeptide material. After two passes through a filter, reductions in vesicle diameter to values in close agreement to filter pore size were observed. These results showed that the charged polypeptide vesicles are readily extruded, allowing good control over vesicle diameter in the tens to hundreds of nanometers range (FIG. 1). Dynamic light scattering (DLS) size analysis revealed that the extruded vesicles were also less polydisperse than before extrusion and contained no micellar contaminants. The vesicular morphology was also confirmed through TEM imaging of the sub-micron $K_{60}L_{20}$ suspensions. The extruded vesicles were monitored for 6 weeks using DLS and were found to be stable since the average diameters did not change for most samples. The vesicles were also found to have high thermal stability. An aqueous suspension of 1 μm vesicles was held at 80° C. for 30 minutes, after which no vesicle disruption could be detected (E. P. Holowka, D. J. Pochan, and T. J. Deming, J Am Chem Soc 127, 12423 (2005)). Only after heating to 100° C. for 30 minutes were the vesicles disrupted, yielding large flat membrane sheets.

Stability of these highly charged polypeptide vesicles in ionic media is important for use in most applications ranging from personal care products to drug delivery. Although the $K_{60}L_{20}$ vesicles are unstable and cluster at high salt concentrations (>0.5 M), they are stable 100 mM PBS butter as well as serum-free DMEM cell culture media (E. P. Holowka, D. J. Pochan, and T. J. Deming, J Am Chem Soc 127, 12423 (2005)). Addition of serum, which contains anionic proteins, results in vesicle disruption, most likely due to polyion complexation between the serum proteins and the oppositely charged polylysine chains. Accordingly, we found that the negatively charged polypeptide vesicles prepared using $E_{60}L_{20}$ are stable in DMEM with 10% fetal bovine serum. Based on these results, we believe these charged polypeptide vesicles show potential as encapsulants for water-soluble solutes as an alternative to liposomes. Another feature of these charged polypeptide vesicles is the potential for facile functionalization of the hydrophilic polypeptide chains at the vesicle surface through either chemical conjugation to anine or carboxylate residues, or by careful choice of charged residues. For example, we recently reported the preparation of arginine-leucine (i.e. $R_{60}L_{20}$) vesicles that are able to readily enter cells due to the many guanidinium groups of the arginine segments (E. P. Holowka et al., Nat Mater 6, 52 (2007)). In this case, the arginine residues played a dual role, where they were both structure directing in vesicle formation, as well as functional for cell binding and entry. The key attributes of block copolypeptides that are advantageous for the design of biomimetic membranes with multifunctional properties are the ability to place structural and functional elements in precise locations within polymer chains. In embodiments of this invention, the copolypeptides populating the interfaces of droplets can also make use of such multifunctional properties, including controlling the morphology and topology of the droplet structures and how they interact with cells and other target materials in applications.

Due to their compartmentalized internal structure, W/O/W double emulsions can provide advantages over simple oil-in-water (O/W) emulsions for encapsulation, such as the ability to carry simultaneously both polar cargoes (such as water-soluble molecules or water dispersable colloids in the inner water droplet) and nonpolar cargoes (such as oil-soluble molecules or oil dispersable colloids in the outer oil droplet), deliver combination therapies of oil-soluble and water-soluble drug molecules to a very specific localized region (e.g. through targeting moieties on molecules that decorate the outer an inner surfaces of the droplets), as well as improved control over temporal release of therapeutic molecules (Pays, K. et al. Double emulsions: how does release occur? *Journal of Controlled Release* 79, 193-205 (2002); Davis, S. S. & Walker, I. M. Multiple Emulsions as Targetable Delivery Systems. *Methods in Enzymology* 149, 51-64 (1987); Okochi, H. & Nakano, M. Preparation and evaluation of W/O/W type emulsions containing vancomycin. *Advanced Drug Delivery Reviews* 45, 5-26 (2000)). The preparation of double emulsions typically requires mixtures of surfactants for stability, and the formation of double nanoemulsions, where both inner and outer droplets are sub-100 nm, has never before been achieved (Garti, N. Double emulsions—Scope, limitations and new achievements. *Colloids and Surfaces A—Physicochemical and Engineering Aspects* 123, 233-246 (1997); Loscertales, I. G. et al. Micro/nano encapsulation via electrified coaxial liquid jets. *Science* 295, 1695-1698 (2002); Utada, A. S. et al. Monodisperse double emulsions generated from a microcapillary device. *Science* 308, 537-541 (2005)).

While offering certain advantages over ordinary O/W emulsions, stable W/O/W emulsions generally do not form spontaneously using a single surfactant and standard emulsification methods according to conventional methods (Garti, N. Double emulsions—Scope, limitations and new achievements. *Colloids and Surfaces A—Physicochemical and Engineering Aspects* 123, 233-246 (1997); Morais, J. M., Santos, O. D. H., Nunes, J. R. L., Zanatta, C. F., Rocha-Filho, P. A. W/O/W Multiple emulsions obtained by one-step emulsification method and evaluation of the involved variables. *Journal of Dispersion Science and Technology* 29, 63-69 (2008)). Microfluidics can be used to make double emulsions that are microns in size and highly uniform (Loscertales, I. G. et al. Micro/nano encapsulation via electrified coaxial liquid jets. *Science* 295, 1695-1698 (2002); Utada, A. S. et al. Monodisperse double emulsions generated from a microcapillary device. *Science* 308, 537-541 (2005)), yet the throughput can be low compared to commercial processes for making polydisperse single emulsions (Mason, T. G., Wilking, J. N., Meleson, K., Chang, C. B. & Graves, S. M. Nanoemulsions: formation, structure, and physical properties. *Journal of Physics—Condensed Matter* 18, R635-R666 (2006)). Typical methods for making W/O/W emulsions involve a two-step process of first forming an 'inverse' water-in-oil (W/O) emulsion, followed by emulsification of this mixture in water using a combination of surfactants (Ficheux, M. F., Bonakdar, L., Leal-Calderon, F. & Bibette, J. Some stability criteria for double emulsions. *Langmuir* 14, 2702-2706 (1998); Wang, Y. F., Tao, Z. & Gang, H. Structural evolution of polymer-stabilized double emulsions. *Langmuir* 22, 67-73 (2006); Garti, N. Double emulsions—Scope, limitations and new achievements. *Colloids and Surface A—Physicochemical and Engineering Aspects* 123, 233-246 (1997); Goubault, C. et al. Shear rupturing of complex fluids: Application to the preparation of quasi-monodisperse water-in-oil-in-water double emulsions. *Langmuir* 17, 5184-5188 (2001); Okushima, S., Nisisako, T., Torii, T. & Higuchi, T. Controlled production of monodisperse double emulsions by two-step droplet breakup in microfluidic devices. *Langmuir* 20, 9905-9908 (2004)). This process allows control of both inner and outer droplet volumes if the emulsions in both stages are monodisperse, yet this process has not been used to form stable nanoscale droplets (i.e. having both inner and outer droplet diameters that are nanoscale). Moreover, this approach requires a difficult search for surfactant combinations that can co-exist without destabilizing either inner or outer droplet interfaces (Ficheux, M. F., Bonakdar, L., Leal-Calderon, F. & Bibette, J. Some stability criteria for double emulsions. *Langmuir* 14, 2702-2706 (1998)). Consequently, there is a need for improving stability against evolution of the droplet sizes (e.g. through coalescence and/or coarsening) and reducing droplet sizes in the development of double emulsions for applications (Benichou, A., Aserin, A., Garti, N. Double emulsions stabilized with hybrids of natural polymers for entrapment and slow release of active matters. *Advances in Colloid and Interface Science* 108-109, 29-41 (2004)).

SUMMARY

An emulsion according to an embodiment of the current invention includes a substantially continuous liquid medium, and a plurality of droplet structures dispersed within said substantially continuous liquid medium. Each droplet structure of the plurality of droplet structures according to this embodiment of the current invention includes an outer droplet of a first liquid having an outer surface; an inner droplet of a second liquid within the first droplet, the second liquid being immiscible in the first liquid, wherein the inner and outer droplets have a boundary surface region therebetween; an outer layer of block copolymers disposed on the outer surface of the outer droplet; and an inner layer of block copolymers disposed on the boundary surface region between the outer and the inner droplets. The block copolymers include a hydrophilic polymer block and a hydrophobic polymer block that act in combination to stabilize the droplet structure, and the first liquid is immiscible in the substantially continuous liquid medium.

An emulsion according to an embodiment of the current invention includes a liquid medium and a plurality of nano-droplets dispersed within the liquid medium. Each of the plurality of nano-droplets includes an inner droplet of a first liquid surrounded by a second liquid, the first liquid being immiscible in the second liquid and the second liquid being immiscible in the liquid medium. The plurality of nano-droplets have an ensemble average diameter of at least about 10 nm and less than about 200 nm.

An emulsion according to an embodiment of the current invention includes a substantially continuous liquid medium and a plurality of droplet structures dispersed within the substantially continuous liquid medium. Each droplet structure of the plurality of droplet structures includes a droplet of a liquid having an outer surface, and a layer of block copolymers disposed on the outer surface of the droplet. The block copolymers comprise a hydrophilic polymer block and a hydrophobic polymer block that act in combination to stabilize the droplet structure, and the liquid of the plurality of droplet structures is immiscible in the substantially continuous liquid medium.

A method of producing an emulsion according to an embodiment of the current invention includes providing a first liquid and a second liquid, the first liquid being immiscible in the second liquid; adding a selected quantity of block copolymers to at least one of the first and second liquids; and emulsifying the first liquid in the second liquid to produce a plurality of droplets of the first liquid dispersed in the second liquid. The block copolymers stabilize said plurality of droplets from coalescing.

A method of producing an emulsion according to an embodiment of the current invention includes at least one of adding a surfactant to at least one of a first liquid and a second liquid, or adding surfactant precursors to at least one of the first liquid and the second liquid; emulsifying the first liquid in the second liquid to form a plurality of droplets of the first liquid immersed in the second liquid to provide a simple emulsion, the first liquid being immiscible in the second liquid; adding at least one of the same surfactant or the same surfactant precursors to a third liquid; and emulsifying the simple emulsion in the third liquid to form a plurality of droplets of the simple emulsion to provide a double emulsion, the second liquid being immiscible in the third liquid. The plurality of droplets of the double emulsion each comprises at least one droplet of the first liquid therein.

BRIEF DESCRIPTION OF THE DRAWINGS

Additional features of this invention are provided in the following detailed description of various embodiments of the invention with reference to the drawings. Furthermore, the above-discussed and other attendant advantages of the present invention will become better understood by reference to the detailed description when taken in conjunction with the accompanying drawings, in which:

FIG. 4A shows laser confocal scanning microscopy (LCSM) images of 0.1 mM FITC labeled $K_{40}rL_{10}$ emulsion (total oil volume fraction $\phi$=0.20, 10 cSt PDMS silicone oil) prepared using an ultrasonic tip homogenizer (Bar=5 µm). FIGS. 4B-4D are emulsions prepared using a microfluidic homogenizer (75 µm interaction chamber). (B) Cryo-TEM image of a $K_{40}rL_{10}$ emulsion: N=6, p=130 psi, C=1 mM and $\phi$=0.20 (Bar=100 nm). (C) Cryo-TEM image of the plug isolated by ultracentrifugation of a $K_{40}rL_{20}$ emulsion: N=6, p=130 psi, C=1.5 mM and $\phi$=0.20, (Bar=100 nm). (D) Remnant suspension of smaller double nanoemulsions obtained by ultracentrifugation and separation of a $K_{40}rL_{20}$ emulsion: N=6, p 130 psi, C=1.5 mM and $\phi$=0.20, (Bar=100 nm).

(FIG. 9A) Photograph of emulsions containing toluene as the oil phase using $K_{60}L_{20}$ and $K_{40}(rac-L)_{20}$ surfactants created using an ultrasonic homogenizer for 1 minute with block copolypeptide concentrations C=0.1 mM, and oil volume fractions $\phi$=0.20. The image was taken 3 hours after emulsification, where the $K_{60}L_{20}$ sample showed noticeable phase separation (oil layer at top). (FIG. 9B) Photograph of attempted emulsification of PDMS silicone oil and water using the homopolypeptide $K_{60}$ as a surfactant. This sample rapidly and completely phase separated, indicating that the homopolymer polypeptide $K_{60}$ did not provide adequate stabilization of oil-water interfaces and any droplets that were transiently produced during the excitation rapidly coalesced after that excitation was ceased.

(FIG. 10A) Plot of measured average diameter of double droplet structures vs. $K_{40}(rac-L)_{20}$ block copolypeptide concentration C. (FIG. 10B) Plot of measured average diameter vs. oil volume fraction $\phi$. (FIG. 10C) Plot of average diameter of double droplet structures vs. hydrophobic (rac-L) length obtained by varying x in different samples of $K_{40}(rac-L)_x$.

(FIG. 11A) Fluorescence microscopy image of W/O/W double emulsions stabilized using fluorescently dyed FITC-$K_{60}(rac-L)_{20}$ containing multiple inner water droplets (note that the L-block is racemic): C=0.1 mM, PBA oil volume fraction $\phi$=0.20 created using an ultrasonic tip homogenizer for 10 seconds. (FIG. 11B) Fluorescence microscopy image of single O/W emulsions stabilized with FITC-$K_{60}L_{20}$ (note that the L block is not racemic): C=0.1 mM, PBA oil volume fraction $\phi$=0.20 created using an ultrasonic tip homogenizer for 10 seconds. (FIG. 11C) CTEM image of nanoscale W/O/W double emulsion droplets with multiple inner water droplets prepared with PBA as the oil phase. (FIG. 11D) CTEM image of nanoscale double emulsion droplets using 300 cSt PDMS (identical viscosity to PBA) as a control oil phase where single inner aqueous droplets are dominant. Emulsion samples for (11C) and (11D) were prepared with $K_{60}(rac-L)_{20}$ using a microfluidic homogenizer (75 μm interaction chamber) under the following conditions: number of passes N=6, homogenizer inlet air pressure p=130 psi, block copolypeptide concentration C=1.0 mM, and oil volume fraction $\phi$=0.20. Scale bars: (11A) and (11B)=5 μm; (11C) and (11D)=100 nm. PBA=bis[3-(acetamido)-propyl] terminated polydimethylsiloxane (number-weighted molecular weight $M_n$=2,500, and viscosity 300 cSt).

(FIG. 12A) CTEM image of a $K_{40}(rac-L)_{20}$ stabilized W/O/W double emulsion. (FIG. 12B) CTEM image of a $K_{60}L_{20}$ stabilized single O/W emulsion. (FIG. 12C) CTEM image of size-fractionated droplets isolated from a $K_{40}(rac-L)_{20}$ stabilized double emulsion by low speed centrifugation followed by ultracentrifugation (using a Beckman ultracentrifuge with SW28 swinging bucket rotor and typical speeds from about 3,000 to about 25,000 RPM). All bars=200 nm.

(FIG. 13A) FITC-labeled $K_{40}(rac-L)_{10}$ stabilized water-in-oil-in-water double emulsion loaded with both pyrene (blue fluorescence) in the outer oil droplets and quantum dots in the inner water droplets (red fluorescence). (FIG. 13B) FITC-labeled $K_{60}L_{20}$ stabilized oil-in-water emulsion loaded with pyrene (blue fluorescence) in the oil droplets. Because $K_{60}L_{20}$ forms a direct emulsion, no red fluorescence is seen within the droplets, confirming the absence of inner water droplets for this particular composition. Both scale bars are 5 μm.

DETAILED DESCRIPTION OF VARIOUS EMBODIMENTS

Figures 1A, 1B, 1C, 1D:
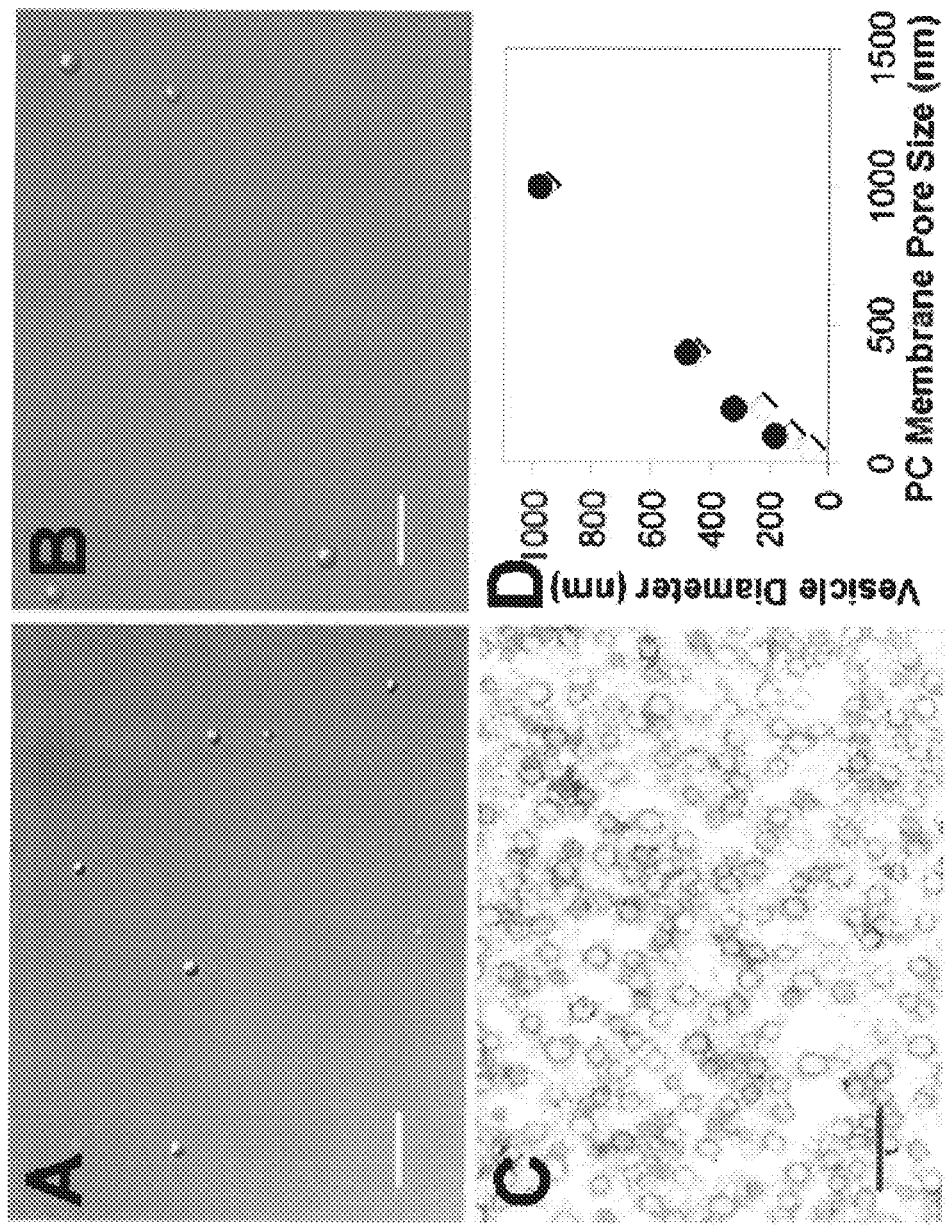
FIGS. 1A and 1B show optical micrographs using differential interference contrast (DIC) of 1% (w/v) suspensions of polypeptide vesicles extruded through 1.0 µm polycarbonate (PC) membranes (Bars=5 µm). (A)=$K_{60}L_{20}$ and (B)=$E_{60}L_{20}$.
FIG. 1C shows TEM image of a uranyl acetate negatively stained 0.1% (w/v) $K_{60}L_{20}$ vesicle suspension filtered through a 0.1 µm PC membrane (Bar=350 nm).
FIG. 1D shows the average diameter of 1% (w/v) aqueous suspensions of vesicles of $K_{60}L_{20}$ (filled circles) and $E_{60}L_{20}$ (open diamonds) as a function of PC membrane pore size. Vesicle diameters were determined using dynamic light scattering (DLS).

Emulsions are dispersions of droplets of one liquid phase material in another immiscible liquid phase material that can be formed, typically through flow-induced rupturing of bigger droplets into smaller ones. A surfactant, which consists of amphiphilic molecules which are surface-active, which is soluble in at least one liquid phase, and which prefers adsorbing on the interfaces between the two immiscible liquids, is usually added in order to prevent subsequent droplet coalescence (i.e. fusion) and to keep the size distribution of the droplets from changing over time. Simple emulsions are generally classified as oil-in-water (i.e. O/W or "direct") and water-in-oil (i.e. W/O or "inverse"), and these different morphologies can be obtained by using an appropriate surfactant that provides adequate stability and can sometimes be influenced through the order of addition of the components while shearing.

The following prefixes: racemic-, r, r-, and rac-, and similar common prefix abbreviations, are used interchangeably to refer to racemic forms of amino acids, oligopeptides, and polypeptide blocks throughout this specification. Likewise, abbreviations cryo-TEM and CTEM are used to refer to cryogenic transmission electron microscopy. The variables p and P are used interchangeably to refer to the same input gas pressure to the microfluidic homogenizer, and φ and (are used interchangeably to refer to the total oil volume fraction.

Oil-in-water emulsions comprised of microscale droplets are common products and have been made for centuries. A simple example is mayonnaise, typically made from egg yolk, which contains both stabilizing amphiphilic lipid and protein molecules, and olive oil that is added in a thin stream while beating the mixture with a whisk or spoon. Some of the mechanical shear energy is stored in the additional droplet interfacial area that is created as the droplets are ruptured down to a smaller size. Typical mechanical devices can produce shear rates that can achieve droplet rupturing down to droplet diameters that are typically around three hundred nanometers, but it is very difficult to achieve a reduction of the peak in the size distribution below this limit. Historically, sub-micron emulsions are known as "mini-emulsions", and these have been created using microfluidic and ultrasonic means for the past twenty years. The term emulsifying used herein is intended to have a broad meaning that can include the process of exciting two immiscible liquids (each of which can include additional components mixed, blended, and/or suspended therein) which are placed in proximity and/or contact, and introducing some form of non-thermal energy to excite and rupture interfacial boundaries between the two liquids in order to form discrete droplets of one immiscible liquid substantially surrounded by the other immiscible liquid. While emulsifying, bigger droplets are typically broken down into smaller droplets (e.g. through interfacial "capillary" instabilities that develop when larger droplets become significantly deformed), thereby forming additional interfacial area. Moreover, while emulsifying, single emulsions, double emulsions, higher-ordered multiple emulsions, and combinations thereof can be formed. The aforementioned methods of emulsifying provide extremely high shear or flow rates that can stretch and rupture even very small droplets. Indeed, there are reports in the literature of the use of ultrasonic dispersers or microfluidic homogenizers that have obtained droplets down into the nanoscale domain: the average droplet sizes are below 100 nm. There is some ambiguity in whether "size" refers to radius or diameter, but this factor of two is a very minor issue, considering the wide range of droplet sizes that can exist from the micellar scale of 2-3 nm all the way up to droplets having macroscopic dimensions.

Here we show that W/O/W double emulsions can be prepared in a simple process and stabilized over many months using single-component, synthetic amphiphilic diblock copolypeptide surfactants according to some embodiments of the current invention. These surfactants even stabilize droplets subjected to extreme flow, leading to direct, mass-production of robust W/O/W double emulsions that have nanoscale inner droplets and also nanoscale outer droplets, and are therefore are amenable to nanostructured encapsulation applications in foods, cosmetics, and drug delivery.

Since amphiphilic diblock polypeptides could function also as surfactants on oil-water interfaces, as well as have properties of self-assembly that reflect their propensity to form vesicles, we have examined the possibility of generating stable double emulsions using minimal shear and a single interfacial agent that is not biased against complex droplet topologies according to some embodiments of the current invention.

We find that it is possible to make direct emulsions and nanoemulsions, as well as double emulsions and double nanoemulsions, stabilized by amphiphilic diblock copolypeptides according to some embodiments of the current invention. Results according to some embodiments of the current invention actually indicate that, for a wide range of molecular weights of the hydrophilic blocks and hydrophobic blocks, the preferred morphology after applying the shear is the double emulsion. Double emulsions can provide a drug delivery vehicle, for example, that can package both water-soluble drugs and oil-soluble drugs. Moreover, the copolypeptide that stabilizes the double emulsion droplets can also be engineered and tailored to provide desirable biochemical interactions, such as biological cell targeting, cellular and subcellular membrane disruption, and enzymatic functionalities, which can enhance the delivery and performance of drug molecules that may be incorporated into the droplet structure.

Figures 2A, 2B, 2C, 2D:
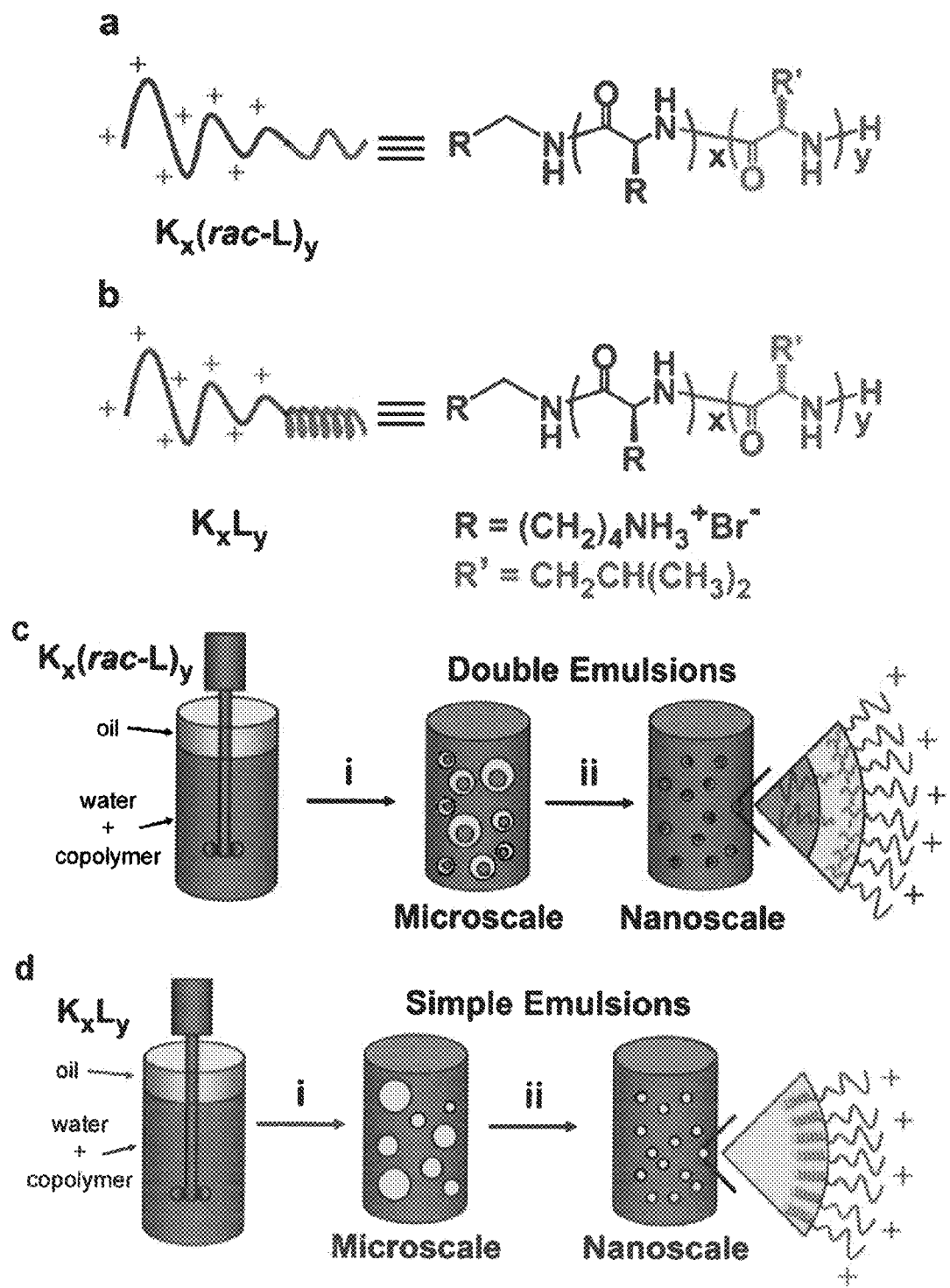
FIGS. 2A and 2B show schematic representative block copolypeptides used for emulsification, $K_xrL_y$ and $K_xL_y$, respectively.
FIG. 2C is a schematic illustration of emulsification processes according to some embodiments of the current invention using $K_xrL_y$ block copolypeptides to generate water-in-oil-in-water double emulsions.
FIG. 2D is a schematic illustration of emulsification processes according to some embodiments of the current invention using $K_xL_y$ block copolypeptides to generate single oil-in-water emulsions. For FIGS. 2C and 2D, step (i) indicates ordinary emulsification such as can be produced using a rotary mixer, to produce microscale droplets, and step (ii) indicates more extreme emulsification, such as can be produced using a microfluidic homogenizer, to produce nanoscale droplets. A detailed section of the interfaces of a resulting droplet structures, showing the copolypeptides at the interlaces, for double and direct emulsions are also illustrated schematically at the right side of FIGS. 2C and 2D, respectively.

A method of producing emulsions, emulsions produced and droplet structures within the emulsions according to some embodiments of the current invention are illustrated schematically in FIGS. 2C and 2D. The method according to an embodiment of the current invention includes providing a first liquid and a second liquid, the first liquid being immiscible in the second liquid, adding a selected quantity of block copolymers to at least one of the first and second liquids, and emulsifying the first liquid in the second liquid to produce a plurality of droplets of the first liquid dispersed in the second liquid. The block copolymers act to stabilize the plurality of droplets against coarsening or other structural evolution that could potentially occur through coalescence or other destabilizing mechanisms. The block copolymers can be, but are not limited to, block copolypeptides. Furthermore, the block copolypeptides can be formed from natural occurring and/or synthetic monomers. The first and second liquids can be an oil (e.g. non-polar) and water (e.g. polar), for example, or vice versa, according to some embodiments of the current invention. However, the invention is not limited to just oil and water as the only pair of immiscible liquids. Other types of polar and non-polar liquid-like materials that are immiscible (e.g. potentially even fluorinated-oils and hydrocarbon-oils that are immiscible) may be used according to other embodiments of the current invention. Therefore, when the terms hydrophobic and hydrophilic are used in this specification and the claims, these terms are more broadly intended to refer to relative differences in molecular interactions between different types of immiscible liquids or immiscible liquid-like materials.

An emulsion according to an embodiment of the current invention can include a substantially continuous liquid medium, and a plurality of droplet structures dispersed within said substantially continuous liquid medium. FIGS. 2C and 2D show two examples of emulsions: double (2C) and direct (2D). However, higher order emulsion can be included according to other embodiments of the current invention. A droplet structure according to an embodiment of the current invention can include an outer droplet of a first liquid having an outer surface, an inner droplet of a second liquid within the first droplet, the second liquid being immiscible in the first liquid, wherein the inner and outer droplets have a boundary surface region therebetween. The droplet structure can also include an outer layer of block copolymers disposed on the outer surface of the outer droplet, and an inner layer of block copolymers disposed on the boundary surface region between the outer and the inner droplets. The term "disposed on" is intended to be a general term which can include, but is not limited to, adsorption onto the surface. For example, the block copolymers may have a portion extending into a portion of the droplet and another portion extending out of the droplet at the surface region, as is illustrated schematically in the droplets on the right hand side of FIGS. 2C and 2D. The term "layer" is intended to be a broad term that includes case in which the block copolymers are loosely arranged around the surface region of the droplet, which can include cases in which the layer is permeable as well as cases in which the layer does not form a completely enclosed surface. The block copolymers can include a hydrophilic polymer block and a hydrophobic polymer block that act in combination to stabilize the droplet structure. The block copolymer layers shown are schematically representative and may not be to scale. The first liquid is immiscible in the substantially continuous liquid medium according to this embodiment of the current invention.

For most compositions that form stable double emulsions, the block copolymer disposed on the interfaces provides a repulsive potential energy of interaction that is significantly stronger than the "thermal energy" corresponding to equilibrium thermal fluctuations, $k_B T$, where $k_B$ is Boltzmann's constant and T is the temperature, between the interfaces of inner droplets and the interfaces of the outer droplets that contain them according to some embodiments of the current invention. In addition, for most compositions that form stable double emulsions, the block copolymer also provides a repulsive potential energy of interaction between the interfaces of outer droplets that encounter other outer droplets that is significantly stronger than thermal energy. For some compositions that form stable double emulsions, the block copolymer can provide a repulsive potential energy of interaction between the interfaces of multiple inner droplets within an outer droplet that is significantly greater than thermal energy. The aforementioned repulsive potential energy of interaction notwithstanding, it is possible for an attractive potential energy of interaction between liquid interfaces to also exist. This attractive potential energy of interaction can lead to aggregation of outer droplets, inner droplets, or a combination thereof in a manner that would not cause coalescence, would not cause film rupturing, and would not destroy the integrity of droplet structures in single, double, and multiple emulsions. Any such attractive potential of interaction may lead to the formation of a secondary minimum in the interaction potential between droplet interfaces, yet this does not necessarily imply that the droplet structures would be destabilized. An example of such an attractive potential energy of interaction is a depletion attraction that may arise between outer droplets as a result of excess copolymer content that may be present in the continuous liquid phase.

For W/O/W double emulsions, although the interfacial stability of an oil film between the surface of the inner water-oil interface and the surface of the outer oil-water interface conferred by adsorbed amphiphilic molecules at the interfaces can be important for ensuring long-term stability of the droplets against evolution of the inner and outer droplet sizes, additional potential factors could influence the long-term stability of the droplets. One potential factor is the potential presence or absence of an osmotic pressure and/or osmotic pressures due to either hydrophilic contents and/or hydrophobic contents of materials loaded into the liquid phases within the double emulsion droplets. For instance, in some methods of producing double emulsions, it is possible for an inner water droplet to contain excess copolypeptide, some of which resides in the water phase of the inner droplet, not just at the water-oil interface at the surface of the inner water droplet. This excess polymer could create an osmotic pressure. Sometimes having such an osmotic pressure created by a water-soluble material and/or water-dispersed material could be desirable for stabilizing droplets against longer-term coarsening processes such as Ostwald ripening. Another potential factor is the potential presence of a soluble material in the continuous water phase outside all of the double droplets that could potentially create an osmotic pressure. Yet another potential factor is the potential presence of an oil-soluble material and/or oil-dispersed material in the outer oil droplets that could potentially create an osmotic pressure. Relative differences in these potential osmotic pressures and the relative solubilities of the oil, water, and other materials in each of the respective other materials can also potentially have an influence on the migration of materials that could potentially change the sizes of inner and outer droplets. The long-term observations we have made for some double emulsion compositions indicate that significant stability of both inner droplet and outer droplet sizes can be achieved in certain embodiments of the current invention.

Concurrent with or subsequent to emulsification of double emulsion droplets, alteration of the liquid material in the inner droplets could be created and used to solidify or otherwise introduce elastic structures in the inner droplet material. Concurrent with or subsequent to emulsification of double emulsion droplets, alteration of the liquid material in the outer droplets could be created and used to solidify or otherwise introduce elastic structures in the outer droplet material. Concurrent with or subsequent to emulsification of double emulsion droplets, alteration of the continuous liquid material outside the double droplets could be created and used to solidify or otherwise introduce elastic emulsion structures in the continuous liquid material. Concurrent with or subsequent to emulsification of double emulsion droplets, alteration of the liquid material of inner droplets, of the liquid material of outer droplets, or of the liquid material of the continuous phase, or a combination thereof, could be created and used to solidify, create structural changes, and/or otherwise introduce elasticity in the double droplet structures. Said alteration could consist of structural changes and/or solidification induced by phase changes (e.g. induced by temperature changes), gelation, crosslinking, polymerization, photopolymerization, chemical reactions, increase in volume fraction of soluble and/or dispersed species (e.g. through transport of lower molecular weight materials in the inner droplet and/or outer droplet), jamming of dispersed species, glassification of dispersed species (e.g. by inducing an attraction between dispersed species), and self-assembly. Likewise, concurrent with or subsequent to emulsification of double emulsion droplets, structural changes that influence the elasticity of a layer of amphiphilic molecules adsorbed at the interfaces of the inner and/or outer droplets could also be altered and controlled. Such alteration might be achieved by selecting amphiphilic molecules that can potentially crosslink to create an elastic layer at the interface of inner droplets and/or outer droplets. Such crosslinking might be induced by electromagnetic radiation, heat, chemical reactions, or a combination thereof.

There are many classes of drug molecules, and the classification can be made in different ways by emphasizing different criteria. Some drug molecules are hydrophobic, some drug molecules are hydrophilic, and some drug molecules even possess a significant degree of amphiphilic nature. By referring to drug molecules, we include all types of molecules that can be used to interact with and affect the viability and function of biological structures and biological entities, including but not limited to biomolecules, sub-cellular structures, biomembranes, cytoplasm, nucleus, extracellular matrix, organelles, cells, synapses, tissues, organs, and organisms.

Drugs, such as drug molecules or formulations of a plurality of drug molecules, that could be introduced into the liquid phases of emulsions, double emulsions, and multiple emulsions include but are not limited to: antiperspirant drugs, anti-itch drugs, anti-infection drugs, anti-inflammatory drugs, anti-arthritis drugs, anti-bursitis drugs, anti-acne drugs, anti-pain drugs, anti-headache drugs, anti-migraine drugs, anti-influenza drugs, anti-depression drugs, anti-diabetes drugs, anti-viral drugs, anti-venin drugs, anti-fungal drugs, anti-(methicillin resistant *staphylococcus aureus*) drugs, anti-biotic drugs, anti-bacterial, anti-microbial, anti-hunger drugs, anti-malnutrition drugs, anti-(acquired immunodeficiency syndrome) drugs, anti-(human immunodeficiency virus) drugs, anti-herpes drugs, anti-hepatitis drugs, anti-spirochete drugs, anti-(Lyme disease) drugs, anti-cholesterol drugs, anti-dandruff drugs, anti-(hair loss) drugs, anti-dermatitis drugs, anti-swelling drugs, anti-addiction drugs, anti-dementia drugs, anti-(Alzheimer's disease) drugs, anti-(Parkinson's disease) drugs, anti-prion drugs, anti-(urinary tract infection) drugs, anti-schizophrenia drugs, anti-hemorrhoid drugs, anti-worm drugs, anti-cancer drugs, anti-seizure drugs, anti-epileptic drugs, anti-manic drugs, anti-anxiety drugs, anti-histamine drugs, ant-coagulant drugs, anti-septic drugs, anti-bacterial drugs, anti-tuberculosis drugs, anti-insomnia drugs, anti-fibromyalgia drugs, anti-incontinence drugs, anti-dermatitis drugs, anti-angiogenesis drugs, anti-allergy drugs, anti-(hay fever) drugs, anti-asthma drugs, anti-(high blood pressure) drugs, anti-(blood clotting) drugs, anti-(motion sickness) drugs, anti-(weight gain) drugs, anti-(weight loss) drugs, anti-obesity drugs, anti-flatulence drugs, anti-burp drugs, anti-constipation drugs, anti-malaria drugs, anti-wart drugs, anti-(skin burn) drugs, anti-(skin sunburn) drugs, anti-(skin wrinkle) drugs, anti-hives drugs, anti-conjunctivitis drugs, anti-(skin boil) drugs, anti-(cold sore) drugs, anti-psychotic drugs, anti-(skin cancer) drugs, anti-eczema drugs, anti-anemia drugs, anti-jaundice drugs, anti-encephalitis drugs, anti-dementia drugs, anti-(premenstrual pain) drugs, anti-chlamydia drugs, anti-protozoan drugs, anti-thrombosis drugs, anti-toothache drugs, anti-earache drugs, anti-tuberculosis drugs, anti-bronchitis drugs, anti-pneumonia drugs, anti-polio drugs, anti-tetanus drugs, anti-(venereal disease) drugs, anti-(attention deficit disorder) drugs, anti-(lip chapping) drugs, anti-osteoporosis drugs, anti-(heart disease) drugs, anti-(heart attack) drugs, anti-(heart failure), anti-stroke drugs, anti-arrhythmia drugs, anti-(peripheral artery disease) agents, anti-platelet agents, anti-anginal drugs, anti-ageing drugs, anti-(memory loss) drugs, anti-hypertension drugs, anti-psoriasis drugs, anti-anorexia drugs, anti-diarrhea drugs, anti-gout drugs, anti-hypothyroid drugs, anti-(organ transplant rejection) drugs, anti-parasite drugs, anti-(erectile dysfunction) drugs, anti-vaginitis drugs, anti-(hot flash) drugs, insect and spider repellants, anesthesia agents, hormones, enzymes, catalysts, inhibitors, promoters, moisturizers, vitality enhancers, skin regeneration agents, skin re-growth agents, hair growth agents, hair re-growth agents, attention enhancers, muscular strength enhancers, male potency enhancers, female fertility enhancers, birth control agents, decongestants, anesthetic agents, ocular treatment agents, smoking cessation enabling agents, nicotine substitution agents, penicillin-related drugs, cephalosporin-related drugs, sulfa-related drugs, mycin-related drugs, endocrine drugs, cardiovascular drugs, pulmonary drugs, central nervous system drugs, gastrointestinal drugs, muscle relaxant drugs, sedative drugs, tranquilizers, hypnotic drugs, analgesic drugs, general anesthetic drugs, vaccines, menopause-related drugs, and diuretic drugs.

Imaging enhancement agents that could be introduced into the liquid phases of emulsions, double emulsions, and multiple emulsions include but are not limited to: magnetic resonance imaging (MRI) enhancement (agents, x-ray computerized tomography (CT) enhancement agents, positron emission tomography (PET) enhancement agents, ultrasound imaging enhancement agents, and optical imaging enhancement agents.

By non-thermal energy, we mean all forms of energy that are not related to equilibrium fluctuations of the constituents of an emulsion system, regardless of whether the emulsion system is a single emulsion or a double emulsion. For instance, out-of-equilibrium imbalances in the local concentrations of constituent materials in an emulsion system could lead to entropic driving stresses that are strong enough to cause droplets of one liquid material to form in another immiscible liquid material without the direct application of external viscous flows. This kind of "spontaneous emulsification" results from local differences in the chemical potential of constituents within the emulsion system that can potentially be strong enough to drive the formation of droplets. Consequently, we regard the restructuring processes giving rise to "spontaneous emulsification" as a form of non-thermal energy, even if there may be some debate about this classification in the prior art. Moreover, "spontaneous emulsification" and other non-equilibrium imbalances in the chemical potential of the species in an emulsion system could also be used to drive the formation of co-polypeptide stabilized double emulsions. Thus, we include entropic driving stresses that lead to spontaneous emulsification and other forms of non-equilibrium transport processes (such as heat- and convection-generating chemical reactions) in what we intend as forms of non-thermal energy.

FIG. 2C shows an example of producing double emulsions according to some embodiments of the current invention. FIG. 2D shows an example of producing single emulsions according to some embodiments of the current invention. The invention is not limited to only direct and double emulsions and is not limited to double emulsions in which droplets have only a single inner droplet. Triple and higher order emulsions are intended to be included within the scope of the current invention. In addition, double emulsions that have one, two or more than two droplets within the larger droplets are included within the scope of the current invention. In the examples of FIGS. 2C and 2D, the double and direct emulsions resulting after step i can be further processed with a microfluidic homogenizer (Microfluidizer® 110S with 75 μm microchannel interaction chamber) to reduce the droplet sizes (e.g. see after step ii in FIGS. 2C and 2D). Various additional processing after the initial emulsification can also be performed within the scope of the current invention.

The amphiphilic block copolypeptides, $K_xrL_y$, where rL (or, equivalently rac-L) signifies a racemic oligoleucine domain, were synthesized using transition metal mediated polymerization of α-amino acid N-carboxy anhydrides (T. J. Deming, Macromolecules 32, 4500 (1999)). The block copolypeptide is composed of a random coil, positively charged poly L-lysine block bound to a racemic oligoleucine block that lacks a stable secondary structure (FIG. 2A). In order to form an emulsion according to an embodiment of the current invention, we began by dissolving a block copolypeptide in water at a desired concentration (C), followed by the addition of oil to give a particular final oil volume fraction ϕ, (FIG. 2C). For copolypeptides typically having racemic hydrophobic blocks, application of shear using a handheld rotary shearing wand (IKA Ultra-Turrax T8 with the S8N-8G dispersing element) formed a microscale premixed emulsion composed of polydisperse (W/O/W) double emulsion droplets ranging in size from 1 to 20 μm (e.g. FIG. 2C after step i). (Note that the double emulsion at this stage was obtained according to this embodiment of the invention without a two-stage emulsification or microfluidic emulsifier as has been described in some conventional processes in the prior art.) This premixed emulsion was then fed into a high-pressure microfluidic homogenizer (e.g. Microfluidizer® Model 110S) typically having an inlet gas pressure p=130 psi (corresponding to liquid pressures in the interaction chamber that are roughly 240 times this inlet gas pressure), which sheared the large droplets into sub-micron and nanoscale droplets (e.g. FIG. 2C after step ii). Optionally, in order to obtain increasingly more monodisperse droplets, the resulting sub-micron and nanoscale emulsion can be re-introduced into the microfluidic homogenizer for N multiple passes, where the integer N is the pass number. This method allows for a straightforward way to produce bulk quantities of sub-micron and nanoscale double emulsion droplets (FIG. 2C). Although for this method of emulsification, we typically perform the emulsifying by using N discrete passes through the microfluidic homogenizer, there are alternative methods of continuous recirculation of the emulsion through the interaction chamber that would also be suitable for performing the emulsifying (i.e. through continuous recirculation emulsification). The use of multiple passes and/or recirculation can have desirable consequences of reducing the overall diameters of the droplet structures and also reducing the polydispersity of the droplet size distributions. In a similar manner, by altering the hydrophobic block of the copolypeptide to be non-racemic by controlling and tailoring the polymer synthesis and then following the same physical emulsification process, direct oil-in-water emulsions that are coated with copolypeptide can also be formed (FIG. 2D).

Figures 3A, 3B, 3C, 3D, 3E, 3F, 3G, 3H:
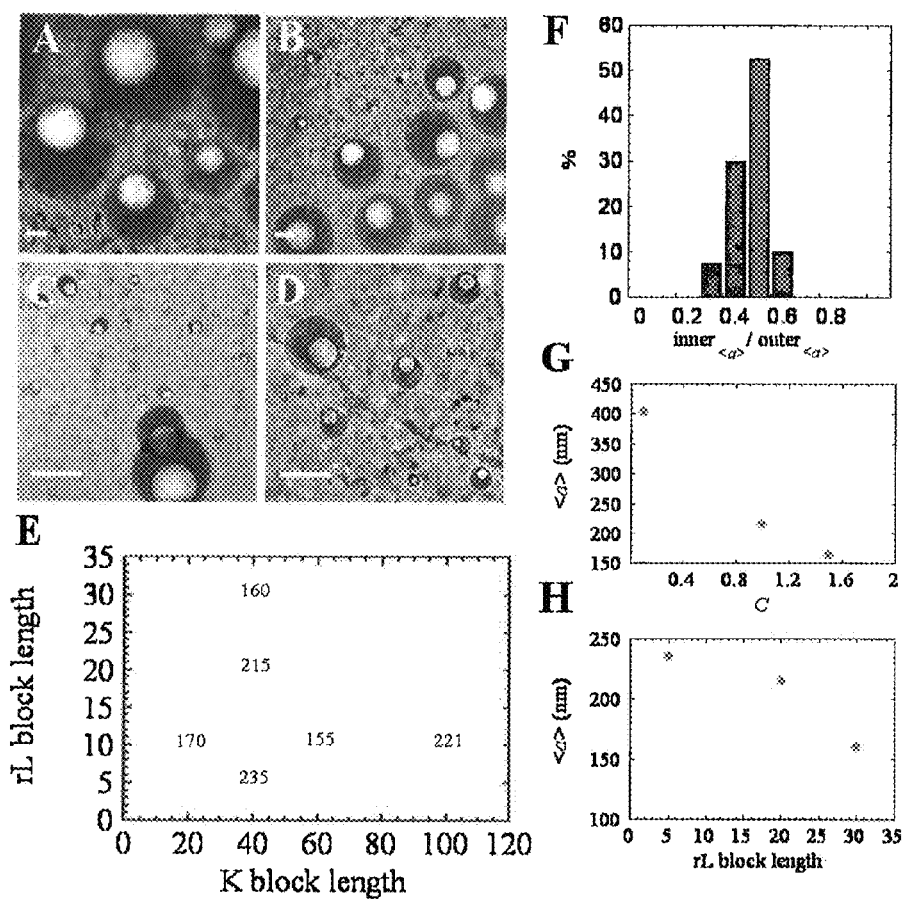
FIGS. 3A-3D show cryogenic transmission electron microscopy (Cryo-TEM) images and dynamic light scattering (DLS) data for $K_xrL_y$ block copolypeptide double emulsions prepared using a microfluidic homogenizer (Microfluidics Microfluidizer® 110S equipped with 75 µm channel dimension interaction chamber). All emulsions were prepared under the following conditions: number of discrete passes through microfluidic homogenizer N=6, input air pressure to microfluidic homogenizer p=130 psi, copolypeptide concentration in water C=1 mM and total oil volume fraction $\phi$=0.20. The oil is polydimethylsiloxane (PDMS) silicone oil having 10 cSt viscosity. Droplet radii from DLS data were determined using cumulant analysis. Cryo-TEM images of $K_xrL_y$ emulsions (Bars=100 nm), (A)=$K_{40}rL_5$, (B)=$K_{40}rL_{10}$, (C)=$K_{40}rL_{20}$, and (D)=$K_{40}rL_{30}$.
FIG. 3E shows the measured effective droplet radii (near the outer droplet radii) of double emulsions by DLS (in nanometers) as a function of the length of the K and rL blocks in the copolypeptide.
FIG. 3F is a histogram (i.e. probability distribution) of the ratio of inner to outer droplet radii for $K_{40}rL_{10}$ measured from Cryo-TEM images.
FIG. 3G shows average droplet radius, <a> (nm) as a function of block copolymer concentration C in (mM) for $K_{40}rL_{10}$. This concentration corresponds to the aqueous phases in which this copolypeptide is soluble.
FIG. 3H shows average droplet radius, <a> (nm) as determined by DLS, as a function of racemic-leucine (rL) block length at a fixed $K_{40}$ block length.

Cryogenic transmission electron microscopy (cryo-TEM or CTEM) can be used to observe and image unperturbed droplet structures in both double and direct emulsions that have been rapidly vitrified in ice without having to introduce staining agents. The images show that double emulsions are indeed formed for a variety of $K_xrL_y$ polypeptide surfactants at 1.0 mM (FIGS. 3A-D). Also, in the cryo-TEM images of $K_{40}rL_{20}$ and $K_{40}rL_{30}$ in particular, there exists a large population of droplets having diameters of about 100 nm and smaller (FIGS. 3C and 3D, respectively). This is surprising given the relatively low concentration of block copolypeptide in solution. In addition, the emulsions produced according to this embodiment of the current invention show some interesting trends concerning the structure of the inner droplet. For many liquid and copolypeptide compositions passed through the microfluidic homogenizer, only one inner aqueous droplet is formed per oil droplet. The efficiency of this process can be very high (>95%). From these images (FIGS. 3A-D), there is a relatively consistent ratio of inner to outer droplet radius for all double droplets in these samples. A histogram detailing the probability of observing a dimensionless ratio (i.e. "I/O ratio") given by: the radius of the inner droplet $a_i$ divided by the radius of the outer droplet $a_o$ containing it, is shown in FIG. 3F. The histogram shows a consistent average value of about $<a_i/a_o> \approx 0.5$ (i.e. 50%) corresponding to a monomodal peak for a $K_{40}rL_{10}$ emulsion (FIG. 3F). Indeed, although there are variations in $a_i$ and $a_o$ from droplet to droplet, this average ratio of $<a_i/a_o> \approx 0.5$ also was observed for some other compositions of double emulsions that have been imaged. In addition, dynamic light scattering (DLS) results of the hydrodynamic radii for emulsions made using a variety of block copolypeptides confirm that sub-micron droplets are formed for a large range of block copolypeptide compositions (FIGS. 3E, 3G, and 3H).

Figures 4A, 4B, 4C, 4D, 4E, 4F:
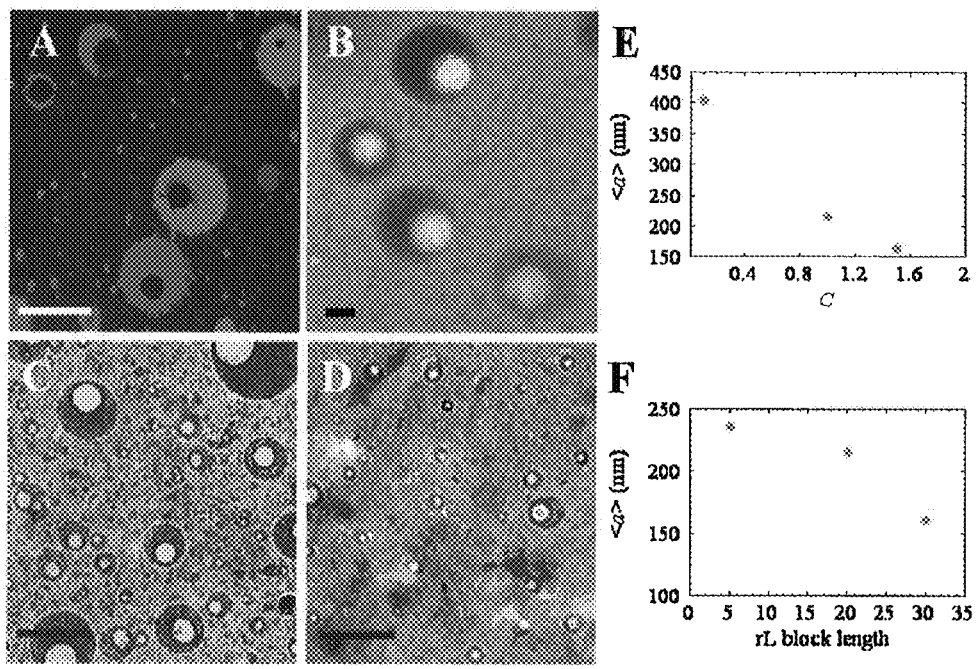
FIGS. 4A-4D show images detailing methods to tune the sizes of W/O/W double emulsion droplets.
FIG. 4E shows average droplet radius, <a> or $K_{40}rL_{20}$ emulsions, determined by DLS as a function of copolypeptide concentration: N=6, p=130 psi, C=0.1 to 1.5 mM and $\phi$=0.20.
FIG. 4F shows average droplet radius, <a>, of $K_{40}rL_y$ determined by DLS as a function of racemic-leucine (rL) block length, y, for: N=6, p=130 psi, C=1 mM and $\phi$=0.20.

Control of the droplet size can be an important issue for drug delivery applications. There are three main means of controlling the size of our double emulsions according to some embodiments of the current invention. One method relies on manipulation of the emulsification conditions through the energy of the non-thermal excitation (e.g. applied shear and extensional flow stresses), the flow properties of the liquids (e.g. viscosity or viscoelasticity), and the interfacial tension between the liquids. A second method involves performing size separations after emulsification, such as centrifugation, filtering, and sorting of droplets in preformed emulsions. A third method varies the composition and concentration of the block copolypeptides through synthesis. Indirectly, this third method also provides a means of varying important physical properties, such as solubility of the copolypeptides in the liquids, the interfacial tension between the liquids in the presence of adsorbed copolypeptide, the viscosity of the liquid solutions containing co-polypeptide, the structural morphology of each of the blocks of the copolypeptide that may confer interfacial stability that preserves droplet stability and inhibits interfacial coalescence. Although we use a chemical process to synthesize the copolypeptides, control over the production of copolypeptides could be achieved through other means, such as genetic expression in bioreactors containing genetically modified bio-organisms. We have the ability to not only produce small double emulsion droplets (with submicron outer droplets and even smaller inner droplets), as discussed previously, but also larger double emulsion droplets (>1 μm). Micron scale emulsion droplets could be made using low flow rates obtained from a handheld homogenizer or somewhat higher flow rates via ultrasonic homogenization (e.g. using an ultrasonic tip homogenizer). When ultrasonic homogenization was used to emulsify a 0.1 mM FITC labeled $K_{40}rL_{10}$ copolypeptide emulsion, laser scanning confocal microscopy (LCSM) demonstrated that we could form larger double emulsion droplets in the size range from 1 μm to 20 μm (FIG. 4A). In addition, we can take this solution of larger double emulsion droplets and further emulsify it into smaller double emulsion droplets by passing it through a microfluidic homogenizer (FIG. 4B).

For certain applications, further size separation may be desired. For these applications, we could also use centrifugation to fractionate the emulsion and isolate emulsions of a desired size range. To accomplish such separation, a 1.5 mM $K_{40}rL_{20}$ emulsion ($\phi$=0.2) that had been passed through the microfluidic homogenizer for six passes (N=6) was placed in a desktop centrifuge set to a low speed of 3,500 rpm (revolutions per minute) for 4 hours. Due to the differences in mass densities of the droplet structures with respect to the continuous liquid phase, the larger droplets rose to the top as a plug more rapidly and could be separated out easily from the extremely dilute suspension of smaller droplets below (i.e. the remnants). We were able to separate out larger droplets that had diameters greater than 300 nm. The remnant suspension had droplet diameters less than 300 nm, therefore, a higher speed centrifuge was needed to further fractionate the sizes of the droplets. The remnant suspension was placed in an ultracentrifuge and centrifuged for 24 hrs at 20,000 rpm. The cryo-TEM images of these layers showed that the droplet sizes can be segregated to a very narrow size range (FIGS. 4C and 4D). A plug formed on top of the centrifuged sample and images showed that the diameter of the outer droplets ranged from about 30 nm to about 200 nm (FIG. 4C), and the remnant suspension had outer droplet diameters ranging from about 10 nm to about 30 nm (FIG. 4D). This fractionation procedure demonstrates that isolation of emulsion droplets of a desired size between 10 nm and 10 μm is quite feasible. Through this centrifugation procedure, we have also demonstrated that it is possible to raise the volume fraction of oil droplets in O/W emulsions and also oil droplets containing inner water droplets in W/O/W double emulsions without destabilizing either inner or outer droplet interfaces.

Another means for controlling double emulsion droplet size was through variation of the block copolypeptides. A simple way to do this was by changing polypeptide concentration. Dynamic light scattering (DLS) results showed that as the $K_{40}rL_{20}$ copolypeptide concentration was increased from 0.1 mM to 1.5 mM the average droplet radius decreased from about 400 nm at 0.1 mM to about 160 nm at 1.5 mM. Another way to decrease the size of the emulsion droplet was to increase the length of the oligoleucine segment in a copolymer. As the oligoleucine length was increased from $K_{40}rL_5$ to $K_{40}rL_{30}$, while holding the lysine length the same ($K_{40}$), the size of the outer oil droplets decreased oil average from about 470 nm to about 320 nm.

Figures 5A, 5B:
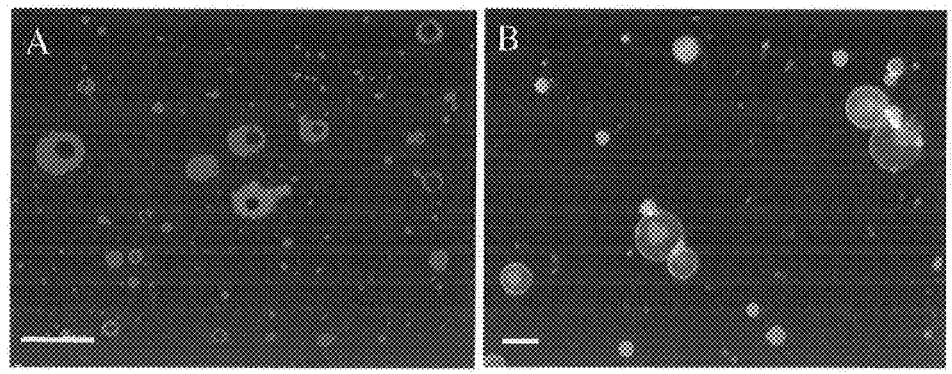
FIG. 5A shows an LCSM image of a FITC labeled 0.1 mM $K_{40}rL_{10}$ double emulsion ($\phi$=0.20, 10 cSt PDMS silicone oil) prepared using a ultrasonic tip homogenizer (10 sec, Bar=5 µm). The FITC-labeled copolypeptide fluoresces green.
FIG. 5B shows multi-color fluorescence micrograph overlay of a FITC labeled C=0.1 mM $K_{40}rL_{10}$ double emulsion prepared using a ultrasonic homogenizer (10 sec) with 0.01 M pyrene (fluoresces blue) in the outer droplets of 10 cSt silicone oil ($\phi$=0.20), and nanoscale InGaP/ZnS quantum dots (fluoresce red) in the inner aqueous droplets (Bar=5 µm).

Vesicles are composed of lamellar membranes that separate an inner aqueous compartment from all outer continuous liquid, where the inner liquid can serve as a container for hydrophilic cargoes. In a similar fashion, double emulsions encapsulate an inner aqueous droplet using a relatively thick oil film that exists between layers of amphiphilic molecules that are present at two distinct oil-water interfaces. One advantage in this system can be that the thicker oil film (which we also refer to as an 'oil layer') located between the interfaces of the inner and outer droplets can act as a reservoir for a hydrophobic cargo. To verify this idea, we incorporated both water-soluble and oil soluble fluorescent markers into our copolypeptide stabilized emulsions. The water-soluble fluorescent markers were InGaP/ZnS quantum dots with an emission wavelength at 630 nm (red), and the hydrophobic fluorescent marker was pyrene due to its high solubility in silicone oil and its blue fluorescence. In addition, by using a green-fluorescently labeled FITC functionalized $K_{40}rL_{10}$ copolymer to stabilize the emulsion, we could simultaneously image localization of both hydrophilic and hydrophobic markers as well as the copolypeptide. Fluorescence LSCM imaging of a 0.1 mM FITC labeled $K_{40}rL_{10}$ emulsion without pyrene or quantum dots showed large double emulsion droplets in the range from about 1 μm to about 5 μm diameters (FIG. 5A). A triple labeled emulsion was made by emulsifying 0.1 mM FITC labeled $K_{40}rL_{10}$ with 0.01 M pyrene in 10 cSt silicone oil ($\phi$=0.2) in the presence of the InGaP/ZnS quantum dots. The 3 different fluorescent dyes were imaged using fluorescence overlay microscopy. The overlayed fluorescence image shows the segregation of the hydrophilic quantum dots (red) into the inner aqueous liquid, the hydrophobic pyrene (blue) into the oil liquid, and the FITC labeled polypeptide (green) stabilizing the outer interface (FIG. 5B). The labeling of the inner droplet interfaces cannot be seen likely due to quenching of the fluorescence of the FITC labeled polypeptide by the quantum dots contained in the inner droplets. Supporting this hypothesis, FITC fluorescence around the inner droplet can be seen in the LCSM image of the FITC-$K_{40}rL_{10}$ emulsion without quantum dots (FIG. 5A).

Figures 6A, 6B, 6C, 6D, 6E:
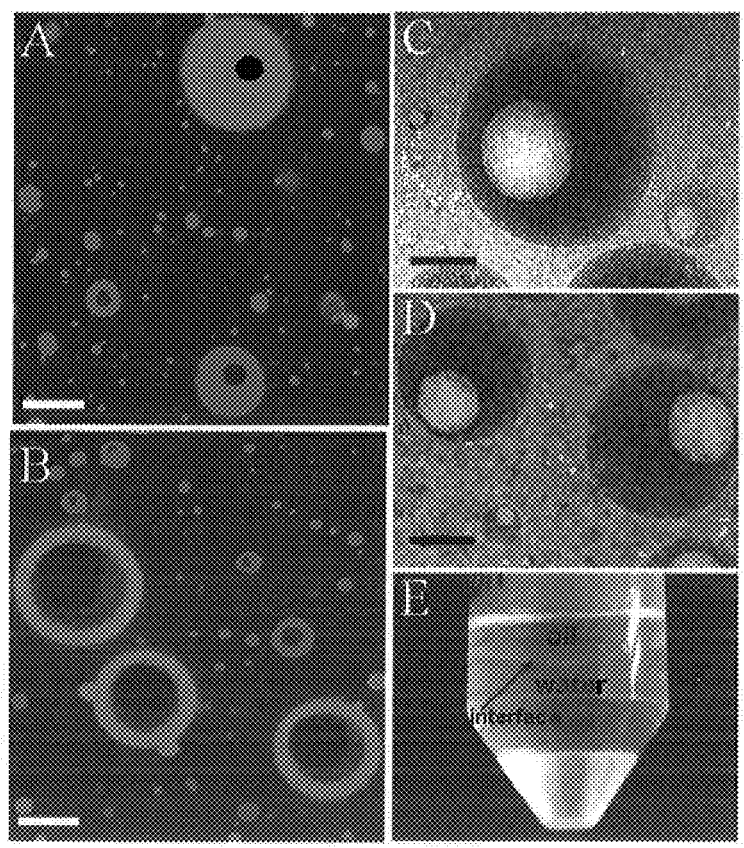
FIGS. 6A-6B show LCSM images of FITC labeled 0.1 mM copolypeptide double emulsions ($\phi$=0.20, 10 cSt PDMS silicone oil) prepared using an ultrasonic tip homogenizer (10 sec). (A)=$K_{60}L_{20}$, (B)=$K_{40}rL_{10}$.
FIG. 6C shows a cryo-TEM image of a 1.0 mM $E_{40}rL_{10}$ emulsion prepared using a microfluidic homogenizer: N=6, p=130 psi, C=1 mM and $\phi$=0.20 (Bar=250 nm).
FIG. 6D shows Cryo-TEM image of a 1.0 mM $K_{40}rL_{10}$ prepared using a microfluidic homogenizer: N=6, p=130 psi, C=1 mM and $\phi$=0.20 (Bar=250 nm).
FIG. 6E shows a photograph of phase separation of silicone oil and water due to non-emulsification of the oil with the water-soluble $K_{60}$ homopolymer polypeptide after similar attempts to make emulsions and/or double emulsions using similar external excitation at similar polypeptide concentrations and total oil volume fractions as in the other panels.

Utilizing our synthetic methods, we can alter the compositions and conformations of our copolypeptides, and also incorporate other amino acids into the polypeptide chains. To demonstrate the effects of changing chain conformations, we altered the hydrophobic domain from a randomly copolymerized racemic oligoleucine segment, as in $K_{40}rL_{10}$, to an enantiomerically pure oligoleucine segment that adopts a stable α-helical structure, as in $K_{60}L_{20}$. LCSM images of the emulsions produced from ultrasonication of both of these FITC-labeled polypeptides at 0.1 mM showed that both samples formed similar double emulsions (FIGS. 6A and 6B). It is also important to note that double emulsion formation is not exclusive to block copolypeptides containing poly L-lysine as the hydrophilic block, but can also form with negatively charged poly L-glutamate hydrophilic segments, for example. A 1.0 mM $E_{40}rL_{10}$ copolypeptide emulsion was prepared using a microfluidic homogenizer. The cryo-TEM images of this sample showed that double emulsions were formed similar to those with the block copolypeptide $K_{40}rL_{10}$ (FIGS. 6C-6D). In addition, emulsification was attempted using the homopolymer $K_{60}$, containing no hydrophobic domain, and no emulsion was formed after ultrasonication (FIG. 6E). Although $K_{60}$ has good solubility in water, one would not expect it to have strong amphiphilic properties, since it lacks a hydrophobic block. We also allowed aqueous solutions of $K_xrL_y$ copolypeptides to remain in contact with oil layers, to see if spontaneous formation of double emulsions occurs without the application of shear. Spontaneous formation was not seen after a one-week incubation period.

Additional Features and Variations:
Copolypeptide-Stabilized Emulsions

There are many potential compositional variations that can be used with the basic process that we have found to make both simple and double emulsions comprised of droplets having microscale, sub-microscale, and nanoscale radii. The basic elements of the process according to some embodiments of the current invention are: a first liquid (e.g. water), a different second immiscible liquid (e.g. oil), and amphiphilic co-polypeptides that have significant solubility in at least one or possibly even both of the two liquids (e.g. soluble in water). The co-polypeptide is added into at least one of the liquids in which it is soluble, and non-thermal energy is supplied to the system of liquids and copolypeptides to disturb interfaces between the two liquids, resulting in irreversible net growth of the interfacial surface area through the formation of droplets and the creation of a metastable emulsion. This applied non-thermal energy can be supplied in many different forms, including a mechanical shear flow, through ultrasonic waves, electromagnetic fields and waves, gravity, concentration gradients, or through a pressure drop that causes extensional flow. As interfaces between the liquids are extended by the non-thermal energy that is introduced to cause emulsification, the interfaces can become unstable to capillary instabilities, causing larger droplets or films to break down into smaller droplets. Depending upon the type of liquids and the composition and structure of the copolypeptide used to stabilize the interfaces, these smaller droplets may or may not contain inner droplets of the other liquid phase (e.g. form W/O/W double emulsions).

To load the inner droplets of W/O/W double emulsions with desired cargo, prior to emulsification, the continuous liquid phase can contain many different kinds of desired dissolved and dispersed cargo elements prior to the emulsification. In the most common case that we have investigated, the continuous liquid phase is water. In this case, the following kinds of cargo could be loaded into the aqueous inner droplets (and also the continuous aqueous phase): single-stranded DNA, double-stranded DNA, single-stranded RNA, double-stranded RNA, mRNA, tRNA, rRNA, miRNA, siRNA, piRNA, rasiRNA, tasiRNA, hcRNA, scnRNA, RNA polymerases, nucleotides, oligonucleotides, transposons, peptides, oligo-peptides, poly-peptides, proteins, microtubules, actin filaments, intermediate filaments, bundling proteins, crosslinking proteins, transfection agents, salts, anions, cations, acids, bases, buffers, viruses, vitamins, serums, lysates, ATP and GTP (e.g. molecular energy sources), molecular motors, hydrophilic drug molecules, cells, vesicles, nanodroplets, nanoemulsions, fullerenes, single and multi-walled carbon nanotubes, cytoplasm, ribosomes, enzymes, glucose, golgi, dendrimers, surfactants, lipids, lipoproteins, oligonucleotide-peptide copolymers, globulins, albumins, human serum albumin, bovine serum albumin, sugars, emulsans, saccharides, oligo-saccharides, poly-saccharides, biocompatible polymers, biodegradable polymers, quantum dots, clay nanoparticles, metal nanoclusters and nanoparticles, magnetically responsive iron oxide nanoparticles, organic and inorganic nanospheres and nanoparticles, isotopically substituted hydrophilic molecules, imaging enchantment agents, and fluorescent dyes. Mixtures of these components in the continuous phase can also be made, provided that they remain stably dispersed. For W/O/W double emulsions stabilized by amphiphilic co-polypeptides, a wide range of hydrophilic materials and water-dispersed materials that are smaller than the final droplet size (or can be compressed into a volume that is less than the inner water droplet volume) and that prefers to be in the aqueous phase can potentially be incorporated into the inner water droplets.

In the case of W/O/W double emulsions, the composition of dispersed materials in the inner water droplets is determined by the composition of the aqueous liquid prior to the application of non-thermal energy that disturbs the interfaces between the liquids (i.e. emulsification). After the emulsification, the inner water droplets will contain the same components that are in the outer continuous water portion. After the emulsification is over, the outer water portion can be separated from the droplets and retained, since it may have valuable components in it. Following this separation, the double emulsion can be re-dispersed in a different continuous aqueous liquid containing block copolypeptide and possibly also another surfactant that would be suitable for maintaining the stability of the droplets over long periods of time in a desired product. In this manner, the composition of the continuous aqueous liquid and that of the inner water droplets (i.e. inside the oil droplets) can be set differently: the inner water droplets can contain the desired drug molecules and particles at the desired concentration, whereas the continuous aqueous liquid does not have to contain them.

The second immiscible liquid (e.g. oil) can also contain a wide array of different molecular, polymer, and particulate materials. Assuming that the second liquid is hydrophobic (e.g. oil), then the following could be incorporated into the dispersed droplet liquid: fats, lipids, waxes, natural oils, essential oils, fragrances, cholesterol, steroids, hydrophobic drug molecules, hydrophobic polymers, hydrophobic polypeptides, poly-(lactic acid), poly-(lactic-co-glycolic acid), poly-(lactic-glycolic acid), biocompatible polymers, biodegradable polymers, micelles, quantum dots, nanoparticles, nanoclusters, carbon nanotubes, fullerenes, ferrofluids, imaging enhancement agents, fluorescent dyes, and liquid crystals. In the case of a W/O/W double emulsion, the oil could contain oil-soluble drug molecules and indicators that would surround the inner water droplet and potentially facilitate and/or improve the desired function of the contents of the water droplet in a cooperative manner.

The liquid portions of the emulsions and/or droplets may be changed to solid or liquid crystalline portions after the emulsion is formed. If a polymerizable oil is used (e.g. ultraviolet crosslinkable silicone oil), then the oil can be made into a rigid crosslinked polymer by illuminating the emulsion or double emulsion with ultraviolet light. Alternatively, if the oil is paraffinic, then cooling the emulsion or double emulsion, once formed, below the solidification temperature of the paraffin would enable the liquid oil to become solidified.

The ability to form stable emulsions and double emulsions is not limited to 10 cSt PDMS silicone oil. We have found that other silicone oils having kinematic viscosities in the range from about 0.65 cSt to 1,000 cSt at room temperature, corresponding to viscosities in the range from about 1 cP to about 1,000 cP also form stable emulsions and stable double emulsions. Other embodiments of the current invention could extend this range of viscosities from about 0.1 cP to more than 10,000 cP. Since heating liquids generally lowers their viscosities, emulsification at hot temperatures could conceivably be used to obtain desired emulsion compositions (e.g. higher viscosity oils) and structures (e.g. reduced droplet sizes). Also, natural oils can be emulsified with our copolypeptides, including soybean oil and methyl oleate. Organic solvents, such as toluene, dichlorobenzene, and dodecane, have also been emulsified in a continuous phase of water using block copolypeptides.

We are able to produce stable droplets in O/W emulsions and stable double droplets in W/O/W double emulsions using oil volume fractions $\phi$ ranging from the extremely dilute limit (e.g. $10^{-5}$) to the concentrated regime above 0.9. Typically, for forming an O/W emulsion or for forming a W/O/W double emulsion the emulsification is carried out for $\phi<0.5$, and more usually O/W emulsions and W/O/W double emulsions are made at $\phi\approx0.1$ to $\phi\approx0.2$. Using a higher $\phi$ can increase the throughput of the droplet production in the emulsification process, so this can be desirable, yet the average dimensions of the droplet structures can also depend on $\phi$, too. The inner droplet radii and volume fractions can also be varied over a wide range. We are also able to make normal direct emulsions and double emulsions over a wide range of radii from the microscale to the nanoscale.

Many different kinds of equipment and devices can be used to supply the energy that disturbs the interfaces in order to create the emulsion or double emulsion: colloid mills, mixers, stirrers, homogenizers, ultrasonic dispersers, magnetic dispersers, electromagnetic dielectrophoretic excitation, microfluidic devices, and porous membrane extrusion. Our studies indicate that, for co-polypeptide stabilization, a variety of different methods can be used to provide non-thermal energetic excitations that disturb the interfaces, and, provided the energy is sufficient to significantly disturb the interfaces, the same emulsion morphology results. We have shown that W/O/W double emulsions can be produced with the same composition including co-polypeptide using stirrers, ultrasonic dispersers, and microfluidic homogenizers.

The following describes in more detail experimental procedures used for the above-noted examples.

General Methods and Materials Tetrahydrofuran (THF) was dried by passage through a column packed with alumina under nitrogen prior to use (A. B. Pangborn et al., Organometallics 15, 1518 (1996)). Molecular weights were obtained by tandem gel permeation chromatography/light scattering (GPC/LS) performed at 60° C. oil a SSI pump equipped with a Wyatt DAWN EOS light scattering detector and Wyatt Optilab DSP. Separations were effected by $10^5$, $10^4$, and $10^3$ Å Phenomenex 5 μm columns using 0.1 M LiBr in DMF as eluent and polypeptide concentration of approximately 5 mg/mL. Infrared spectra were recorded on a Perkin Elmer RX1 FTIR Spectrophotometer calibrated using polystyrene film. $^1$H NMR spectra were recorded on a Bruker AVANCE 400 MHz spectrometer. Deionized (DI) water was purified using a Purelab Option 560 reverse osmosis purifier. Millipore water was obtained from a Millipore Milli-Q Biocel A10 purification unit. Silicone oil (poly-(dimethylsiloxane) or PDMS) is supplied by Gelest, Inc. with viscosities ranging from 1 cSt to 1,000 cSt (corresponding to different average molecular weights of the PDMS).

Block Copolypeptide Synthesis—General

The α-amino acid-N-carboxyanhydride NCA monomers were synthesized using previously published literature protocols (H. R. Kricheldorf, α-*Aminoacid-N-Carboxyanhydrides and Related Materials* (Springer-Verlag, NY, 1987)). All of the block copolypeptides were polymerized using the $(PMe_3)_4Co$ initiator (H. F. Klein, and H. H. Karsch, Chem. Ber. 108, 944 (1975)). The resulting polypeptides were characterized using GPC, $^1$H NMR and IR spectroscopy (T. J. Deming, Macromolecules 32, 4500 (1999)). The compositions of the copolymers were determined by analysis of the integration values of the $^1$H NMR spectra recorded in $D_2O$. All compositions were found to be within 5% of predicted values. From measured polymer chain length distributions, the polydispersity index (Mw/Mn) ranged from 1.1 to 1.3.

Poly($N_\epsilon$CBZ-L-lysine)$_{40}$-b-poly(rac-leucine)$_{20}$

In the drybox, L-Lysine NCA (10.00 g, 33 mmol) was dissolved in THF (200 mL) and placed in a 500 mL flat bottom flask that could be sealed with a plastic stopper. An aliquot of $(PMe_3)_4Co$ (16 mL of a 48 mg/mL solution in THF) was then added via syringe to the flask. A stir bar was added and the flask sealed and let stir for 45 minutes. An aliquot (50 μL) was removed from the polymerization for CPC analysis (Mn=11,000, Mw/Mn=1.24). L-leucine NCA (1.3 g, 8.2 mmol) and D-Leucine NCA (1.3 g, 8.2 mmol) were dissolved in THF (52 mL) and then added to the polymerization mixture. After stirring for another 16 h, the solution was removed from the drybox and the THF removed under reduced pressure. FTIR analysis showed complete consumption of monomer and was similar to previously reported results (V. Breedveld et al., Macromolecules 37, 3943 (2004)).

Poly(L-Lysine-HBr)$_{40}$-b-poly(rac-Leucine)$_{20}$, $K_{40}rL_{10}$

The poly($N_\epsilon$CBZ-L-lysine)$_{40}$-b-poly(rac-Leucine)$_{20}$ from above was dissolved in trifloroacetic acid (TFA) (350 mL), transferred to a 1 L flat bottom flask and placed into an ice bath. HBr (33% in acetic acid) was then added (40 ml, 131 mmol) and the reaction stirred for 2 hrs. Deprotected polymer was isolated by addition of diethyl ether to the reaction mixture, followed by centrifugation. The isolated polymer was then dissolved in DI water and dialyzed (6,000-8,000 MWCO membrane) against tetrasodium EDTA (3 mmol, 4 days), 0.1 M HCl (2 days), DI water (1 day), 0.1 M LiBr (2 days), DI water (2 days), changing each solution 3 times/day. The dialyzed polymer was isolated by freeze-drying to give the product as a dry white powder (4.8 g, 70.2%). FTIR and $^1$H-NMR were performed and shown to be similar to previous results (V. Breedveld et al., Macromolecules 37, 3943 (2004)).

FITC Functionalized $K_{10}rL_{10}$

The $K_{40}rL_{10}$ copolymer was prepared as described above. GPC analysis of the first segment (poly CBZ-lysine): Mn=10,500, Mw/Mn=1.20. The deprotected copolymer (150 mg, $1.3 \times 10^{-2}$ mmol) was dissolved in water and placed in a 125 mL flat bottom flask. $NaHCO_3$ (162 mg, 19 mmol) was added to the solution. Fluorescein isothiocyanate (FITC) (5 mg, $1.3 \times 10^{-2}$ mmol) was dissolved in dry DMSO (1 mL) and added to the polymer solution. A stir bar was added and the reaction mixture was stirred overnight. The polymer solution was dialyzed (6,000-8,000 MWCO membrane) for 3 days against DI water, changing water 3 times/day. The dialyzed polymer was isolated by freeze-drying to yield a yellow-orange polymer containing approximately 1 fluorescein unit per polymer chain (130 mg, 87%).

Emulsification of Silicone Oil Using $K_{40}rL_{10}$

The freeze-dried $K_{40}rL_{10}$ copolypeptide was first dissolved in de-ionized water at the desired concentration. The range of block copolypeptide concentrations, C, varied from $1.0 \times 10^{-4}$ mM to 1.7 mM. Silicone oil (10 cSt, Gelest PDMS) was added to give the desired volume fraction φ of oil to the continuous phase ($0.01 \leq \phi \leq 0.8$). A premix emulsion was prepared by applying shear using either a handheld homogenizer (IKA Ultra-Turrax T8 with the S8N-8G dispersing element) or a handheld ultrasonic homogenizer (Cole-Palmer 4710 Series Model ASI at an output of 35-40%). This premix emulsion was then passed through a M-110S Microfluidizer® Processor with a 75 μm stainless steel/ceramic interaction chamber and an input air pressure p=130 psi. The emulsion was collected at the product outlet of the microfluidic homogenizer, and then passed through the microfluidic homogenizer five more passes (N=6 total), which decreased the average droplet radius <a> and increased the monodispersity of the sample. We have formed double emulsions of copolypeptide, water, and various oils other than 10 cSt and 100 cSt silicone oil, including soybean oil and methyl oleate. Cryo-TEM has also confirmed the formation of double emulsions using the following copolypeptide compositions: $K_{20}rL_{10}$, $K_{40}rL_5$, $K_{10}rL_{10}$, $K_{40}rL_{20}$, $K_{40}rL_{30}$, $K_{40}rL_{20}$, and $E_{40}rL_{10}$ (E=Glutamic Acid).

Fractionation of Emulsions

A 1.5 mM $K_{40}rL_{20}$ emulsion (prepared as above) was centrifuged in a 15 mL plastic centrifuge tube for 24 h at 3,500 rpm using an IEC HN-S tabletop centrifuge. A 0.5 mm plug formed, and was separated from the remnants. A plug was formed at the top of the tube (droplet sizes >300 nm, by cryo-TEM), due the different densities of silicone oil and water (0.973 g/mL for 10 cSt PDMS silicone oil vs. 1.0 g/mL for water). The plug was isolated from the rest of the sample, designated as primary remnants, and these primary remnants were further fractionated at 20,000 rpm for 4 hrs using a Beckman L8-55 ultracentrifuge. A plug formed on the top of the suspension (droplet sizes ranging from 30 nm to 200 nm, by cryo-TEM) along with droplets remaining in suspension as secondary remnants (droplet sizes ranging from 10 nm to 30 nm, by cryo-TEM).

Dynamic Light Scattering (DLS)

The diameters of emulsion droplets were estimated by dynamic light scattering (DLS) with a Photocor-FC board and software. The samples were diluted to obtain an intensity reading of between $1\times10^5$ and $6\times10^5$. Each measurement was performed at a scattering angle of 90° for 500 seconds, with linear channel spacing and an adjustable baseline. The fitting procedure used was cumulant analysis with an adjustable baseline to fit the data and calculate average droplet radii.

Loading of Three Fluorescent Probes into Different Components of $K_{40}rL_{10}$ Emulsions To label the hydrophobic liquid, we dissolved pyrene in the silicone oil component at a concentration of 0.01 M, quantum dots (Evident Technologies, Type T2-MP 650 nm Macoun Red InGaP/ZnS, amine-functionalized) were dispersed in the water component at a concentration of 2 μM. To prepare the emulsion, FITC-$K_{40}rL_{10}$ (150 μL of an 0.1 mM solution) was combined with InGaP quantum dots (50 μL of an 8 μM solution) and pyrene in 10 cst silicon oil (50 μL of a 0.01 M pyrene solution). The mixture was emulsified using an ultrasonic tip homogenizer (output of 35%) for 10 seconds.

Laser Scanning Confocal Microscopy (LSCM)

A 0.1 mM FITC-$K_{40}rL_{10}$ emulsion ($\phi$=0.2, 10 cSt silicone oil) was prepared by combining 800 μL of a 0.1 mM FITC-$K_{40}rL_{10}$ polypeptide solution and 200 μL of 10 cSt PDMS silicone oil, followed by emulsification for 10 s using a hand-held ultrasonic homogenizer (output of 35%). Prior to imaging, an aliquot of the 0.1 mM FITC-$K_{40}rL_{10}$ emulsion suspension was diluted by a factor of 10 with de-ionized (DI) water. One drop of the emulsion was placed on a glass slide, followed by placement of a cover slip. The samples were imaged using a Leica-SP MP confocal and multiphoton inverted microscope equipped with a 488 nm (blue) argon laser (JDS Uniphase) and a 561 nm (green) diode laser (DPSS: Melles Griot) and a two-photon laser setup consisting of a Spectra-Physics Millenia X 532 nm (green) diode pump laser and a Tsunami Ti:sapphire picosecond-pulsed infrared laser tuned at 768 nm for ultraviolet excitation.

Fluorescence Microscopy

Prior to fluorescence imaging, emulsion suspensions were diluted tenfold with DI water. A drop of emulsion was then placed onto a glass slide and covered using a glass cover slip. The samples were imaged using a Zeiss 200 fluorescence microscope.

Cryogenic TEM Imaging

Each emulsion sample was diluted tenfold with DI water prior to imaging. An aliquot of each sample (5 μL) was then placed on a carbon grid. The grid was loaded into a Vitrobot (FEI) automated vitrification device for automated sample blotting and vitrification in liquid ethane. The grid was stored under liquid nitrogen and then placed, using a cold stage, in a Phillips Tecnai F20 electron microscope with an accelerating voltage of 120 kV. Images were obtained on a Teitz SCX slow-scan CCD detector coupled to the Leginon software package.

ADDITIONAL EXAMPLES

The block copolypeptide surfactants we designed according to some embodiments of the current invention have the general structure poly(L-lysine H Br)$_x$-b-poly(racemic-leucine)$_y$, $K_x$(rac-L)$_y$, where x ranged from 20 to 100, and y ranged from 5 to 30 residues (FIG. 1A). The hydrophilic poly(L-lysine.HBr) segments are highly charged at neutral pH, provide good water solubility (Katchalski, E. & Sela, M. Synthesis and chemical properties of poly-alpha-amino acids. *Advances in Protein Chemistry* 13, 243-492 (1958)), and possess abundant amine groups for chemical functionalization (Niederhafner, P., Sebestik, J. & Ježek, J. Peptide dendrimers. *Journal of Peptide Science* 11, 757-788 (2005)). Unlike hydrophobic segments of other polymeric amphiphiles, poly(L-leucine) segments adopt rod-like α-helical conformations that give rise to strong interchain associations and poor solubility in common organic solvents (Nowak, A. P. et al. Rapidly recovering hydrogel scaffolds from self-assembling diblock copolypeptide amphiphiles. *Nature* 417, 424-428 (2002)). We have shown that block copolymers of the structure $K_xL_y$ (e.g. $K_{60}L_{20}$) associate strongly in water to form membranes via packing of the hydrophobic segments (Holowka, E. P., Pochan, D. J. & Deming, T. J. Charged polypeptide vesicles with controllable diameter. *Journal of the American Chemical Society* 127, 12423-12428 (2005)). Consequently, we have focused on poly(rac-leucine) since its disordered chain conformation improves solubility (Table 1) (Kricheldorf, H. R. & Mang, T. C-13-NMR Sequence-Analysis, 20. Stereospecificity of the Polymerization of D,L-Leu-NCA and D,L-Val-NCA. *Makromolekulare Chemie—Macromolecular Chemistry and Physics* 182, 3077-3098 (1981); Breitenbach, J. W., Allinger, K. & Koref, A. Viskositätsstudien an Lösungen von DL-Phenylalanin-Polypeptiden. *Monatsh. Chem.* 86, 269 (1955)) and helps promote surface activity (Table 1), while its peptidic nature allows for additional mechanical stabilization of droplet interlaces via interchain H-bonding in the oil phase (Lapp, C. & Marchal, J. Preparation De La Poly-D,L-Phenylalanine En Helice Par Polymerisation De La D,L-Benzyl-4 Oxazolidine Dione-2-5. *Journal De Chimie Physique Et De Physico—Chimie Biologique* 60, 756-766 (1963)).

Figures 9A, 9B:
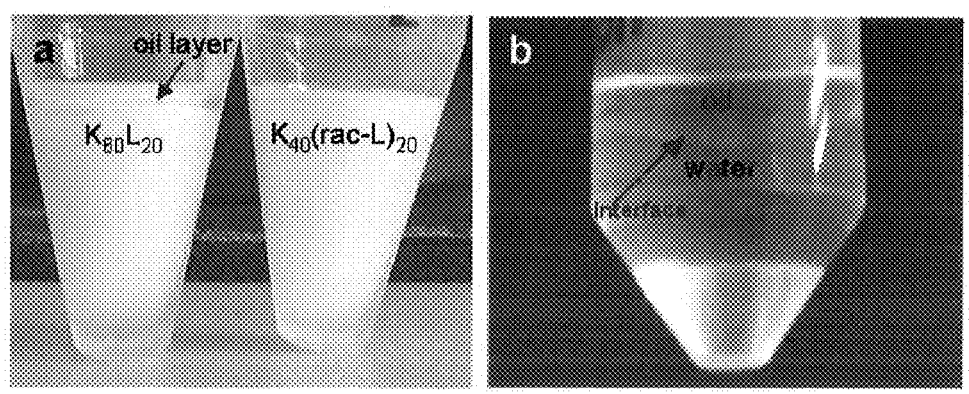
FIGS. 9A and 9B show comparison of emulsification properties of copolypeptides.
Figures 11A, 11B, 11C, 11D:
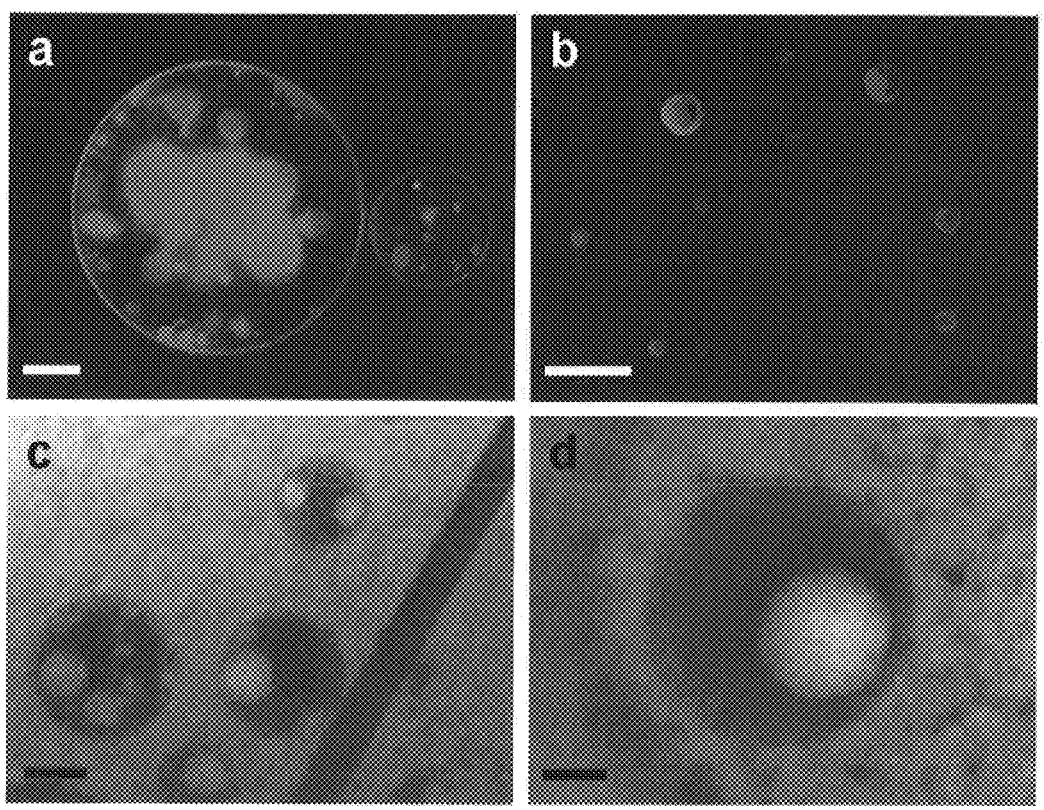
FIGS. 11A-11D are fluorescence microscopy and CTEM images showing influence of silicone oil capped with acetamide groups (PBA) on hydrogen bonding in the oil phase of emulsions.

Diblock copolypeptides were screened for emulsification activity by adding PDMS silicone oil to aqueous $K_x$(rac-L)$_y$ solutions (Table 1, FIGS. 2A-2B, 11A). The resulting mixtures were sheared using a handheld rotary homogenizer and then passed six times through a high-pressure microfluidic homogenizer (FIG. 2C). All $K_x$(rac-L)$_y$ samples gave stable W/O/W nanoemulsions that did not ripen or phase separate for over 9 months. Only copolypeptides with low hydrophobic content, e.g. $K_{40}$(rac-L)$_5$, gave emulsions that slowly phase separated after 1 year. Other methods of mixing, including ultrasonic mixing, also provided stable emulsions, but with droplets having diameters of up to several microns. Use of hydrophobic segments longer than thirty residues greatly diminished aqueous solubility (Table 1), where $K_{40}$(rac-L)$_{30}$ could only be dissolved up to 1 mM. As controls, 0.1 mM suspensions of $K_{60}L_{20}$ and $K_{60}$ were also used as surfactants, where $K_{60}L_{20}$ did form stable emulsions and $K_{60}$ failed to emulsify oil and water mixtures (FIGS. 9A-9B). These results indicated that $K_x$(rac-L)$_y$ surfactants give stable emulsions over a broad range of compositions and concentrations.

Figures 7A, 7B, 7C, 7D:
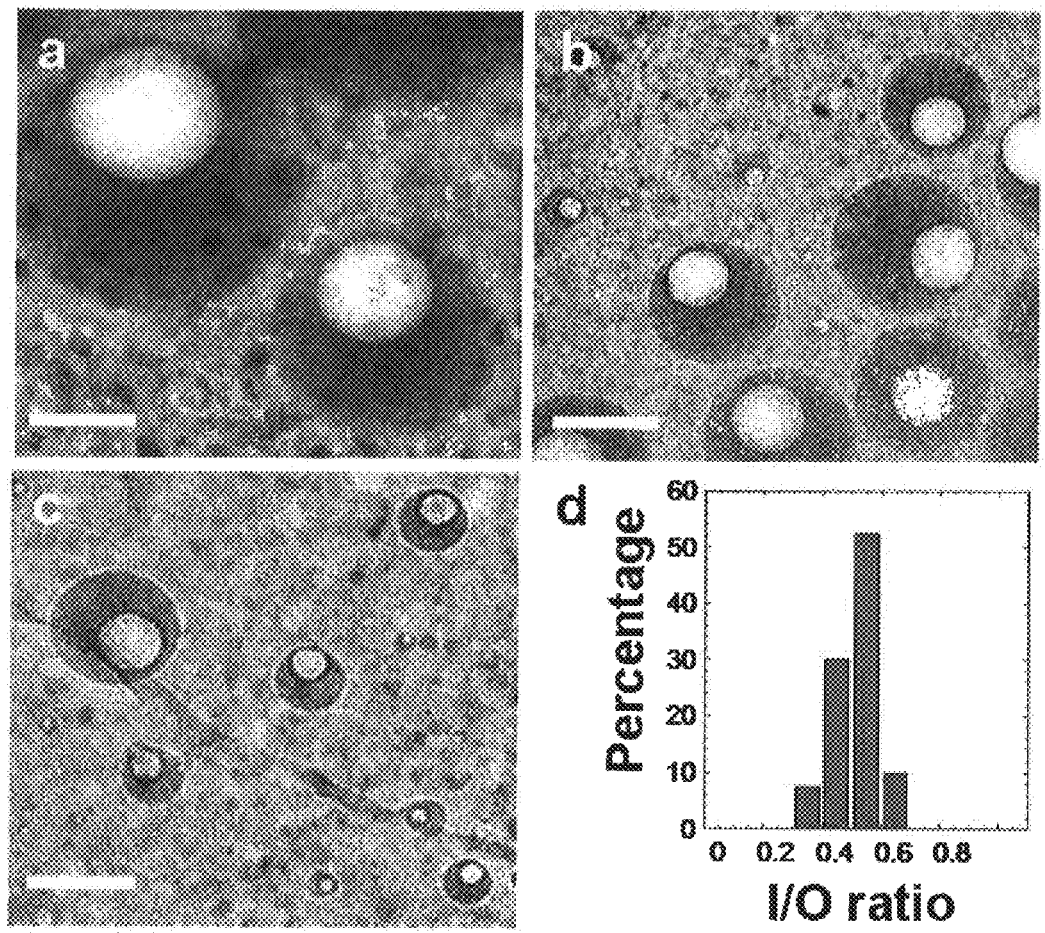
FIGS. 7A-7C show CTEM images for $K_x(rac-L)_y$, stabilized double emulsions prepared using a microfluidic homogenizer under the following conditions: number of passes N=6, homogenizer inlet air pressure p=130 psi, block copolypeptide concentration C=1.0 mM, and total oil volume fraction $\phi$=0.20 (PDMS silicone oil 10 cSt). (Bars=200 nm): (a)=$K_{40}(rac-L)_5$, (b)=$K_{40}(rac-L)_{10}$, and (c)=$K_{40}(rac-L)_{30}$.
FIG. 7D shows a histogram displaying the observed probability distribution (in %) as a function of the ratio of inner radius $a_i$ to outer radius $a_o$ (i.e. I/O ratio) determined by measuring $a_i$ and $a_o$ from at least 50 double emulsion droplets observed in a cryo-TEM image of a $K_{40}(rac-L)_{10}$ emulsion.
Figures 8A, 8B, 8C, 8D:
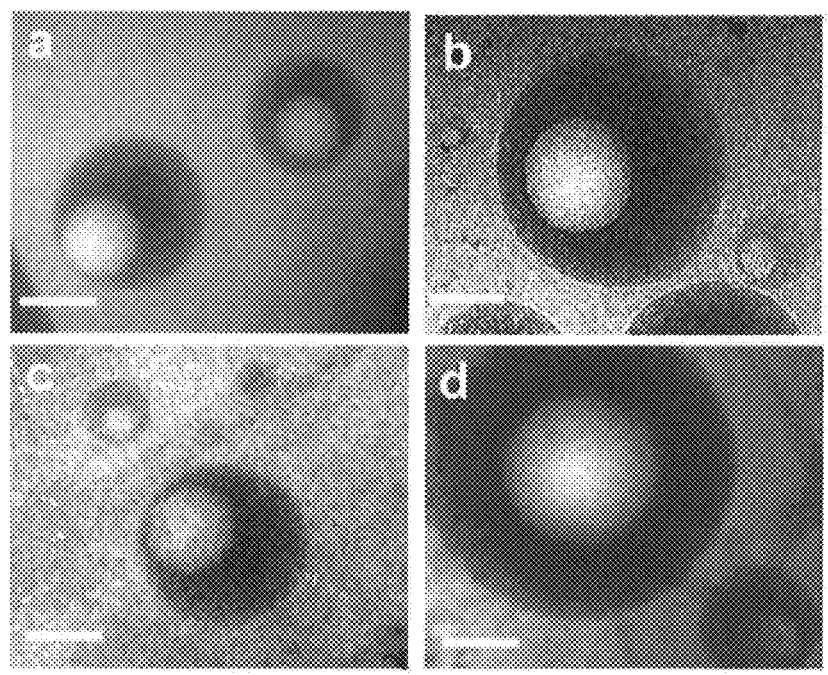
FIGS. 8A-8D show cryo-TEM (CTEM) images of various block copolypeptides used to stabilize double emulsions. CTEM images of (FIG. 8A) $R_{40}(rac-L)_{10}$ (R=L-arginine hydrobromide used in the polymerization) and (FIG. 8B) $E_{40}(rac-L)_{10}$ (E=L-glutamic acid sodium salt used in the polymerization) stabilized double emulsions prepared using a microfluidic homogenizer under the following conditions: N=6, homogenizer inlet air pressure p=130 psi, block copolypeptide concentration C=1.0 mM, and oil volume fraction $\phi$=0.20 (PDMS silicone oil 10 cSt). CTEM images of (FIG. 8C) $K_{60}(rac-V)_{20}$ (V=valine) and (FIG. 8D) $K_{60}(rac-A)_{20}$ (A=alanine) stabilized double emulsions created using an ultrasonic homogenizer for 1 minute with block copolypeptide concentration C=1.0 mM, and oil volume fraction $\phi$=0.20 (PDMS silicone oil 10 cSt). All scale bars=200 nm.
Figures 10A, 10B, 10C:
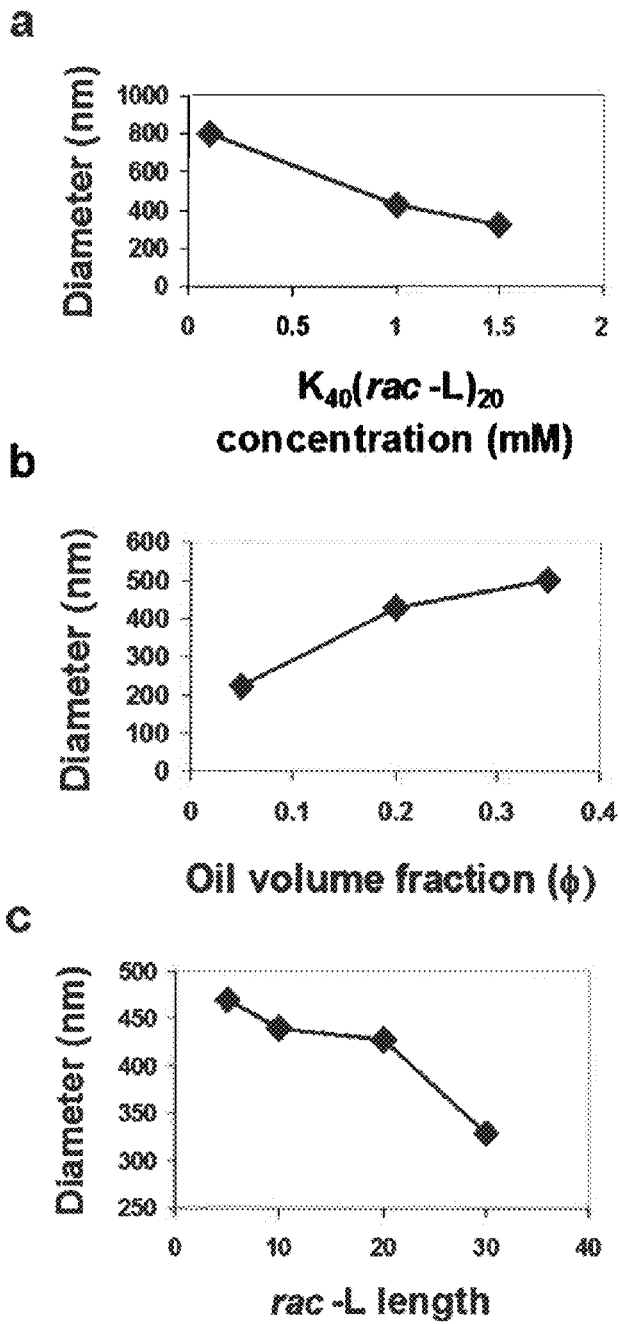
FIGS. 10A-10C are plots of dynamic light scattering (DLS) data showing how double emulsion droplet sizes are affected by different experimental parameters. All samples were prepared using a microfluidic homogenizer (75 μm interaction chamber) under the following conditions: number of passes N=6, homogenizer inlet air pressure p=130 psi. Diameters were determined using cumulant analysis of the (DLS) correlation function and are estimates of average outer droplet diameters of the W/O/W double emulsions.

To probe droplet structure, block copolypeptide stabilized emulsions were imaged using optical microscopy and cryogenic transmission electron microscopy (CTEM). All samples with $K_x$(rac-L)$_y$ were found to contain oil droplets, each containing predominately a single internal aqueous droplet with consistent inner to outer volume ratios (FIGS. 7A-8D). Contrasting these results, the emulsions formed using $K_{60}L_{20}$ contained only simple oil droplets, revealing that the racemic-leucine segments play a key role in stabilizing the double emulsion structure in this embodiment of the current invention. As copolypeptide hydrophobic content was decreased, droplet sizes increased (Table 1, FIG. 10C), suggesting that copolymer composition influences interfacial mean curvature. Average droplet diameters were also found to increase when the concentration of $K_{40}$(rac-L)$_{20}$ was decreased (FIG. 10A). Likewise, decreasing the oil volume fraction yielded smaller emulsion droplets (FIG. 10B). Emulsions always formed such that water remained the continuous liquid and did not invert up to oil volume fractions approaching 50%. In addition to PDMS, other immiscible liquids such as dodecane, soybean oil, and methyl oleate gave emulsions using 1 mM $K_{40}(rac-L)_{20}$ in water. The versatility of various embodiments of the current invention was shown by formation of stable emulsions using $R_{40}(rac-L)_{10}$ or $E_{40}(rac-L)_{10}$, containing guanidinium or carboxylate functionality of L-arginine (R) and L-glutamate (E), respectively (FIGS. 8A-8B).

Figures 12A, 12B, 12C:
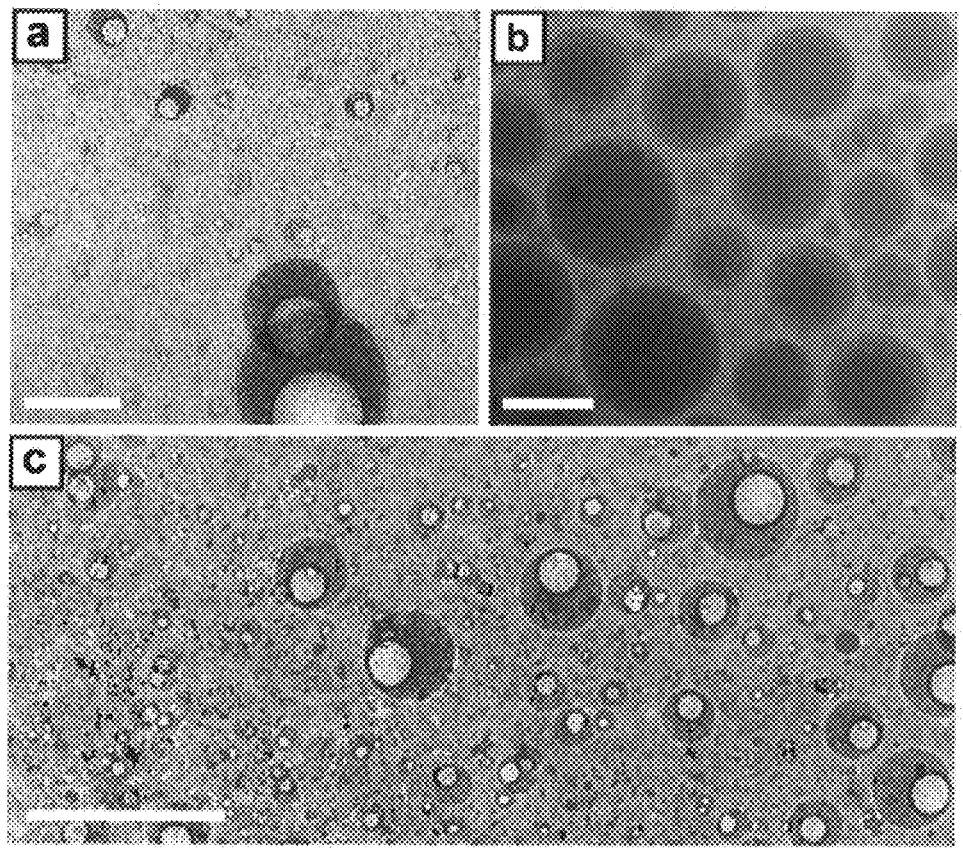
FIGS. 12A-12C show cryogenic transmission electron microscopy (CTEM) images for copolypeptide-stabilized single and double emulsions prepared using a microfluidic homogenizer, showing how the racemic nature of the L-block can influence the type of emulsion generated. Vitrified water gives a lighter background and silicone oil, which has a greater density of higher atomic number atoms, appears darker and provides contrast. Emulsions were prepared under the following conditions: N=6, p=130 psi, C=1.0 mM, and oil volume fraction $\phi$=0.20 (PDMS silicone oil 10 cSt).

Formation of nanoscale emulsion droplets is necessary for many applications, such as drug delivery where the outer droplet diameter generally needs to be less than 200 nm, and preferably between 50 nm and 100 nm (Kataoka, K., Kwon, G. S., Yokoyama, M., Okano, T. & Sakurai, Y. Block-Copolymer Micelles as Vehicles for Drug Delivery. *Journal of Controlled Release* 24, 119-132 (1993)). Although many conventional methods are available for preparation of double emulsions, none allow preparation of outer droplets in this size range (Garti, N. Double emulsions—Scope, limitations and new achievements. *Colloids and Surfaces A—Physicochemical and Engineering Aspects* 123, 233-246 (1997); Loscertales, I. G. et al. Micro/nano encapsulation via electrified coaxial liquid jets. *Science* 295, 1695-1698 (2002); Utada, A. S. et al. Monodisperse double emulsions generated from a microcapillary device. *Science* 308, 537-541 (2005); Benichou, A., Aserin, A., Garti, N. Double emulsions stabilized with hybrids of natural polymers for entrapment and slow release of active matters. *Advances in Colloid and Interface Science* 108-109, 29-41 (2004)). Ultrasonic homogenization was used to prepare a $K_{40}(rac-L)_{20}$ emulsion yielding a polydisperse sample with the smallest double emulsion droplets observed by (TEM being ca. 400 nm in diameter. These droplets were further reduced in size by passage six times through a microfluidic homogenizer, yielding droplet diameters ranging from ca. ten to a few hundred nanometers. The stability of these double emulsions against both external and internal coalescence allowed the use of centrifugation to fractionate droplets into a desired size range. Centrifugation of the sample in FIG. 12A gave a buoyant fraction containing droplets hundreds of nanometers in diameter. The smaller droplets in the remaining suspension were further separated by ultracentrifugation (Mason, T. G., Wilking, J. N., Meleson, K., Chang, C. B. & Graves, S. M. Nanoemulsions: formation, structure, and physical properties. *Journal of Physic-Condensed Matter* 18, R635-R666 (2006)), yielding a fraction with droplets ranging from ca. 10 nm to 100 nm in diameter (FIG. 12C). This fractionation procedure shows that isolation of stable double emulsion droplets in the nanoscale range is quite feasible, and that they are remarkably stable to applied external stresses, such as shear stresses, extensional stresses, and osmotic compressional stresses.

Figures 13A, 13B:
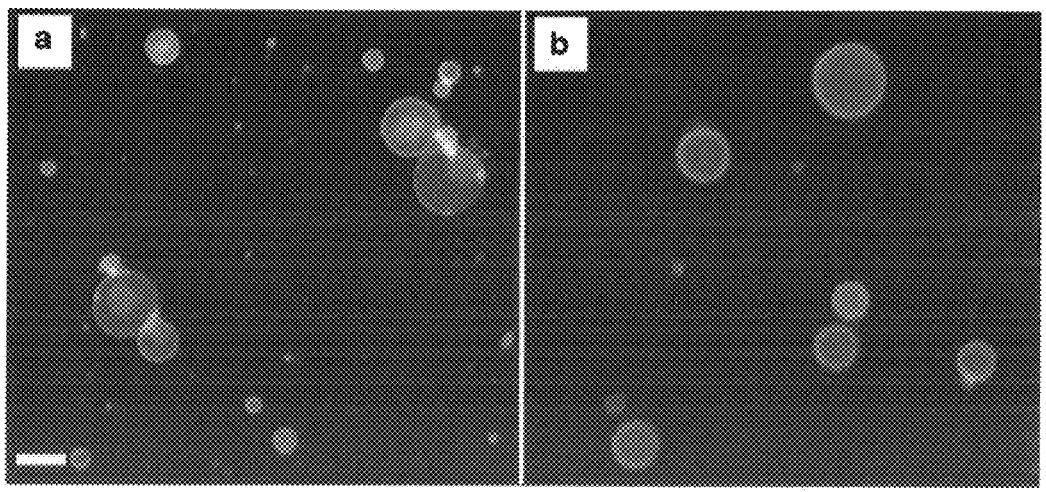
FIGS. 13A and 13B show fluorescence micrographs of double emulsions containing polar and nonpolar cargoes. Samples prepared using an ultrasonic tip homogenizer (10 sec at 35% power) with $\phi$=0.2 and C=0.1 mM. The oil phase fluoresces blue due to entrapped pyrene (0.01 M), and an internal aqueous phase, if present, fluoresces red due to encapsulation of InGaP quantum dots (at concentration of 2 μM). The polypeptides fluoresce green due to labelling with fluorescein (FITC). Before imaging, the droplets were dialyzed against and subsequently diluted with pure water to remove most of the quantum dots and therefore red fluorescence from the external continuous aqueous phase.

To demonstrate their encapsulating ability, both water-soluble and oil soluble fluorescent markers were loaded into copolypeptide stabilized double emulsions. A dispersion of InGaP/ZnS quantum dots was mixed with fluorescein labeled FITC-$K_{40}(rac-L)_{10}$ prior to emulsification with PDMS silicone oil containing pyrene. Using fluorescence microscopy, both markers and the labeled polypeptide were imaged in the double emulsion droplets (FIG. 5B). The images also showed the compartmentalization of hydrophilic quantum dots (red) into the inner aqueous phase, hydrophobic pyrene (blue) into the oil phase, and the labeled polypeptide (green) stabilizing the outer interface. Polypeptide at the inner interface was not observed likely due to quenching of the fluorescein label by the quantum dots. In samples prepared with $K_{60}L_{20}$ surfactant, only simple oil droplets with no internal aqueous compartment were observed (FIG. 13B). These cargoes were observed to remain encapsulated within the droplets for at least 3 months, showing unprecedented enhanced stability of the inner aqueous compartment compared to most double emulsion systems (Davis, S. S. & Walker, I. M. Multiple Emulsions as Targetable Delivery Systems. *Methods in Enzymology* 149, 51-64 (1987); Garti, N. Double emulsions—Scope, limitations and new achievements. *Colloids and Surfaces A—Physicochemical and Engineering Aspects* 123, 233-246 (1997); Benichou, A., Aserin, A., Garti, N. Double emulsions stabilized with hybrids of natural polymers for entrapment and slow release of active matters. *Advances in Colloid and interface Science* 108-109, 29-41 (2004)).

These $K_x(rac-L)_y$ surfactants were designed with high hydrophilic contents (HC), namely the ratio of hydrophilic to hydrophobic residues, which favor stabilization of O/W emulsions where the oil is on the concave side of the curved interface of a nanoscale droplet. Conversely, the inner water-oil interface of a W/O/W double emulsion is best stabilized by a surfactant with a low HC since the oil is on the convex side of the interface. The opposite signs of these mean interfacial curvatures (Strey, R. Microemulsion microstructure and interfacial curvature. *Colloid and Polymer Science* 272, 1005-1019 (1994)) explain why single component surfactants generally do not stabilize double emulsion droplets and, consequently, combinations of surfactants are required (Ficheux, M. F., Bonakdar, L., Leal-Calderon, F. & Bibette, J. Some stability criteria for double emulsions. *Langmuir* 14, 2702-2706 (1998)). This also explains the formation of only O/W emulsions prepared with $K_{60}L_{20}$, since the rod-like oligoleucine segments are poorly solvated by the oil and tend to aggregate in the oil phase (Nowak, A. P. et al. Rapidly recovering hydrogel scaffolds from self-assembling diblock copolypeptide amphiphiles. *Nature* 417, 424-428 (2002)). Based on these observations, it appears that stabilizing an inner aqueous droplet in a W/O/W double emulsion is significantly more likely when the hydrophobic polypeptide segments disperse readily in the oil and thereby prevent steric crowding of the large hydrophilic segments in the aqueous phase.

The racemic-leucine segments in $K_x(rac-L)_y$ provide a combination of features that stabilize double emulsion droplets. The conformational flexibility of these segments improves oil solubility, since it has been shown that poly(rac-leucine) is soluble in organic solvents such as $CH_2Cl_2$ and $(CH_3)_2SO$ whereas poly(L-leucine) is not (Kricheldorf, H. R. & Mang, T. C-13-NMR Sequence-Analysis, 20. Stereospecificity of the Polymerization of D,L-Leu-NCA and D,L-Val-NCA. *Makromolekulare Chemie—Macromolecular Chemistry and Physics* 182, 3077-3098 (1981); Breitenbach, J. W., Allinger, K. & Koref, A. Viskositätsstudien an Lösungen von DL-Phenylalanin-Polypeptiden. *Monatsh. Chem.* 86, 269 (1955)). This allows $K_x(rac-L)_y$ chains to better stabilize an inner droplet oil-water interlace us the hydrophobic segments can disperse more readily in the oil. Despite its improved solubility, in an oil solvent, nearly all residues of poly(rac-leucine) will also be engaged in both intramolecular and intermolecular H-bonds. Studies on racemic polymers of both leucine and phenylalanine have demonstrated that they associate in organic solvents via H-bonding (Lapp, C. & Marchal, J. Preparation De La Poly-D,L-Phenylalanine En Helice Par Polymerisation De La D,L-Benzyl-4 Oxazolidine Dione-2-5. *Journal De Chimie Physique Et De Physico— Chimie Biologique* 60, 756-766 (1963)). At the interface of an inner aqueous droplet with oil, the high HC of our polymers favors a low packing density of rac-leucine segments in the oil phase that would allow few interchain H-bonds and give a weakly stabilized interface (FIG. 2C). However, the opposite curvature of the outer droplet oil-water interface allows dense packing of the racemic-leucine segments in the oil phase, favoring interchain H-bonding. Consequently, even though inner aqueous droplets are likely unstable, they are prevented from merging with the outer droplets, and forming simple emulsions, since the outer interfaces are expected to be reinforced by H-bond crosslinking. To test this concept, emulsions were prepared containing a silicone oil capped with acetamide groups capable of H-bonding to rac-leucine segments. Emulsification with $K_{60}(rac-L)_{20}$ gave W/O/W nanoemulsions containing multiple internal droplets (FIGS. 11A-11D), supporting the hypothesis that rac-leucine segments can stabilize droplets through H-bonding interactions in the oil phase, thus inhibiting internal droplet coalescence.

Our use of racemic, disordered hydrophobic polypeptide segments that interact via H-bonding is a novel means for stabilizing W/O/W double emulsions. This approach differs greatly from protein and peptide stabilized emulsions where double emulsions do not form without use of additional surfactants, and an ordered amphiphilic helix is the most common source of surface activity (Enser, M., Bloomberg, G. B., Brock, C., Clark, D. C. De novo design and structure-activity relationships of peptide emulsifiers and foaming agents. *International Journal of Biological Macromolecules* 12, 118-124 (1990); Dickinson, E. Structure and composition of adsorbed protein layers and the relationship to emulsion stability. *Journal of the Chemical Society Faraday Transactions* 88, 2973-2983 (1992); Saito, M., Ogasawara, M., Chikuni, K., Shimizu, M. Synthesis of a peptide emulsifier with an amphiphilic structure. *Bioscience, Biotechnology and Biochemistry* 59, 388-392 (1995), Dalgleish, D. G. Conformations and structures of milk proteins adsorbed to oil-water interfaces. *Food Research International* 29, 541-547 (1996); Chang, C. B., Knobler, C. M., Gelbart, W. M., Mason, T. G. Curvature Dependence of Viral Protein Structures on Encapsidated Nanoemulsion Droplets. *ACS Nano* 2 281-286 (2008)). Our strategy also can be applied to other copolypeptides, since samples containing rac-valine and rac-alanine hydrophobic segments also gave stable double nanoemulsions (FIGS. 8C, 8D). Use of block copolypeptide surfactants can overcome key limitations of W/O/W double emulsions by allowing the unprecedented straightforward preparation of nanoscale droplets, which also exhibit high stability and can be used to simultaneously encapsulate both oil-soluble and water-soluble cargoes. The term cargo is used to refer to any material that one can add to the liquid contained within any of the droplets, whether these droplets are inner droplets or outer droplets of double emulsions or simple droplets of direct emulsions.)

Methods Summary $K_{40}(rac-L)_{20}$ copolypeptide was first dissolved at the desired concentration (e.g. 0.01 mM<C<1.5 mM) in ultrapure water. PDMS silicone oil (10 cSt) was added to give the desired volume fraction A of oil to the continuous phase (0.05<φ<0.50). A microscale emulsion (i.e. "premix" emulsion) was prepared by either mixing for 1 minute using a handheld homogenizer (IKA Ultra-Turrax T8 with the S8N-8G dispersing element) or by mixing for 10 seconds using a handheld ultrasonic tip homogenizer (Cole-Parmer 4710 Series Model ASI at an output of 35-40%). This emulsion was then passed through a M-110S Microfluidizer® Processor with a 75 µm stainless steel/ceramic interaction chamber and an input air pressure p=130 psi. The emulsion was collected at the product outlet, and then passed through the microfluidic homogenizer repeatedly for a total of six passes (N=6), which decreased the average droplet radius <a> (e.g. of the single droplets in a simple emulsion and of the outer and inner droplets in a double emulsion) and increased the monodispersity of the droplets in the emulsions. A similar protocol was used for emulsions generated using other block copolypeptide surfactants (Table 1. FIGS. 7A-7C). The ratio given by the inner droplet radius divided by the outer droplet radius (labeled as "I/O ratio") was relatively uniform for different hydrophobic chain lengths at approximately 0.5 (Table 1, FIG. 7D). Other amphiphilic block copolypeptides, where either the lysine or leucine domains were substituted with different hydrophilic or hydrophobic residues, respectively, were also found to form double emulsions (FIGS. 8A-8D). The emulsification capability of different polypeptide surfactants was also qualitatively evaluated using toluene, which forms less stable emulsions, and with a control homopolypeptide, $K_{60}$ (FIGS. 9A, 9B), which does no yield stable emulsions or stable double emulsions.

Supplementary Methods

Materials. Tetrahydrofuran (THF) was dried by passage through a column packed with alumina under nitrogen prior to use (Nowak, A. P. et al. Rapidly recovering hydrogel scaffolds from self-assembling diblock copolypeptide amphiphiles. *Nature* 417, 424-428 (2002)). Molecular weights were obtained by tandem gel permeation chromatography/light scattering (GPC/LS) performed at 60° C. on a SSI pump equipped with a Wyatt DAWN EOS light scattering detector and Wyatt Optilab DSP. Separations were effected by $10^5$, $10^4$, and $10^3$ Å Phenomenex 5 µm columns using 0.1 M LiBr in DMF as eluent and polypeptide concentrations of approximately 5 mg/mL. Infrared spectra were recorded on a Perkin Elmer RX1 FTIR Spectrophotometer calibrated using polystyrene film. $^1$H NMR spectra were recorded on a Bruker AVANCE 400 MHz spectrometer. Deionized (DI) water was purified using a Purelab Option 560 reverse osmosis purifier. Ultrapure (18 MΩ) water was obtained from a Millipore Milli-Q Biocel A10 purification unit. Silicone oil (10 cSt, polydimethylsiloxane, PDMS) was supplied by Gelest, Inc.

Figure 14:
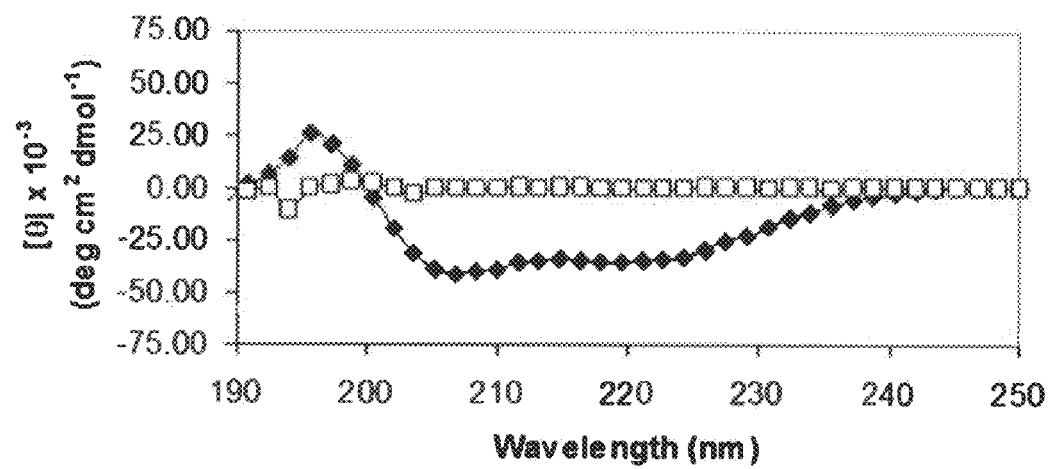
FIG. 14 shows circular dichroism spectra of block copolypeptide solutions (1.0 mg/mL) in ultrapure water. The minima at 208 and 222 nm in the (rac-K)$_{60}$L$_{20}$ sample are characteristic of the α-helical conformation. ♦=(rac-K)$_{60}$L$_{20}$, and □=(rac-K)$_{40}$(rac-L)$_{20}$.

Block Copolypeptide Synthesis. The α-amino acid-N-carboxyanhydride NCA monomers were synthesized using previously published literature protocols (id.). The resulting polypeptides were characterized using GPC, $^1$H NMR and IR spectroscopy (Id.). The compositions of the copolymers were determined by analysis of the integration values of the $^1$H NMR spectra recorded in $D_2O$. All compositions were found to be within 5% of predicted values. Polymer chain length distributions (Mw/Mn) ranged from 1.1 to 1.3. $K_{60}L_{20}$ was synthesized using a published procedure (Holowka, E. P., Pochan, D. J. & Deming. T. J. Charged polypeptide vesicles with controllable diameter. *Journal of the American Chemical Society* 127, 12423-12428 (2005)). Chain conformations of the hydrophobic poly(leucine) segments were confirmed using circular dichroism spectroscopy (FIG. 14), where the contributions from the poly(lysine) segments were removed using poly(racemic-lysine) segments as previously described (Nowak, A. P. et al. Rapidly recovering hydrogel scaffolds from sell-assembling diblock copolypeptide amphiphiles. *Nature* 417, 424-428 (2002)).

Poly($N_ε$-CBZ-L-lysine)$_{40}$-b-poly(rac-leucine)$_{20}$. In a nitrogen filled glove box, CBZ-L-Lysine NCA (10 g, 33 mmol) was dissolved in THF (200 mL) and placed in a 500 mL flat bottom flask that could be sealed with a plastic stopper. An aliquot of $(PMe_3)_4Co$ (16 mL of a 48 mg/mL solution in THF) was then added via syringe to the flask. A stir bar was added, then the flask was sealed and allowed to stir for 45 minutes. An aliquot (50 µL) was removed from the polymerization solution for GPC analysis (Mn=11,000, Mw/Mn=1.24). L-Leucine NCA (1.3 g, 8.2 mmol) and D-Leucine NCA (1.3 g, 8.2 mmol) were dissolved in THF (50 mL) and then added to the polymerization mixture. After stirring for another 16 h, FTIR analysis showed complete consumption of monomer, similar to previously reported results (Id.).

Poly(L-lysine-HBr)$_{40}$-b-poly(rac-leucine)$_{20}$, $K_{40}$(rac-L)$_{20}$. The poly(N$_\epsilon$-CBZ-L-lysine)$_{40}$-b-poly(rac-leucine)$_{20}$ solution from above was removed from the drybox and the THF removed under reduced pressure. The block copolypeptide was then dissolved in trifluoroacetic acid (TFA) (350 mL), transferred to a 1 L flat bottom flask, which was placed into an ice bath. HBr (33% in acetic acid) was then added (40 mL, 131 mmol) and the reaction stirred for 2 hrs. Deprotected polymer was isolated by addition of diethyl ether (400 mL) to the reaction mixture, followed by centrifugation. The isolated polymer was then dissolved in DI water and dialyzed (using a 6,000 to 8,000 MWCO membrane) in a 4 L container against aqueous tetrasodium EDTA (3 mmol, 2 days), aqueous HCl (100 mmol, 2 days), DI water (1 day), aqueous LiBr (100 mmol, 2 days), and finally DI water (2 days), changing each solution 3 times/day. The dialyzed polymer was isolated by freeze-drying to give the product as a dry white powder (4.8 g, 70%). FTIR and $^1$H-NMR were performed oil the block copolypeptide and were found to be similar to previous results (Id.).

FITC functionalized $K_{40}$(rac-L)$_{10}$. The $K_{40}$(rac-L)$_{10}$ copolymer was prepared in a manner similar to $K_{40}$(rac-L)$_{20}$. GPC analysis of the first segment (poly CBZ-L-lysine) gave: Mn=10,500, Mw/Mn=1.20. The deprotected copolymer (150 mg, $1.3 \times 10^{-2}$ mmol) was dissolved in water and placed in a 125 mL flat bottom flask. NaHCO$_3$ (160 mg, 19 mmol) was then added to the solution. Fluorescein isothiocyanate (FITC) (5.0 mg, $1.3 \times 10^{-2}$ mmol) dissolved in dry DMSO (1 mL) was added to the polymer solution. A stir bar was added and the reaction mixture was stirred overnight. The polymer solution was dialyzed (using a 6,000 to 8,000 MWCO membrane) for 3 days against DI water, changing the water 3 times/day. The dialyzed polymer was isolated by freeze-drying to yield a yellow-orange polymer containing approximately 1 fluorescein unit per polymer chain (130 mg, 87%). The FITC functionalized $K_{60}L_{20}$ copolymer was prepared using a similar procedure.

Loading of fluorescent probes into different phases of FITC-$K_{40}$(rac-L)$_{10}$ stabilized double emulsions. To label the hydrophobic phase, pyrene was dissolved in silicone oil at a concentration of 0.01 M. To label the aqueous phase, water soluble quantum dots (Evident Technologies, Type T2-MP 650 nm Macoun Red InGaP/ZnS, amine-functionalized) were dispersed in the aqueous phase at a concentration of 2 µM. To prepare the emulsion, solutions of FITC-labeled $K_{40}$ (rac-L)$_{10}$ (150 µL of a C=0.1 mM solution) and InGaP quantum dots (50 µL of an 8 µM solution) were mixed with pyrene in 10 cSt silicone oil (50 µL of a 0.01 M pyrene solution). The mixture was emulsified using an ultrasonic tip homogenizer (output of 35%) for 10 s. The same procedure was followed for the FITC-$K_{60}L_{20}$ block copolypeptide surfactant. Prior to imaging, the non-encapsulated quantum dots were removed by dialysis against deionized water.

The invention has been described in detail with respect to various embodiments, and it will now be apparent from the foregoing to those skilled in the all that changes and modifications may be made without departing from the invention in its broader aspects, and the invention, therefore, as defined in the claims is intended to cover all such changes and modifications as fall within the true spirit of the invention.

For example, it can be desirable to make W/O/W double emulsions at higher oil volume fractions φ. Double emulsions can be routinely formed through emulsification at φ ranging from dilute volume fractions φ<<1 up to φ≈4 of the primary dispersed phase of the outer droplet, and, through simple and appropriate modifications of the procedures, up to about φ≈0.6 in some embodiments. It is conceivable that certain particular embodiments that extend this known regime could achieve φ>0.6, up to about φ≈0.9. After emulsifying at a particular φ, droplet structures (including simple single droplets and also double droplets) can be subsequently concentrated to higher φ by applying osmotic stresses through methods including evaporation, dialysis, centrifugation, ultracentrifugation, filtration, and microfluidic concentration. The maximum volume fraction to which the emulsion can be concentrated and still remain stable can depend on many factors, including the droplet sizes and how the copolymers stabilize the elastic interfaces. For certain embodiments, the concentration can be achieved up to φ≈0.95. For nanoscale droplets, reaching volume fractions of up to about φ≈0.8 through concentration processes subsequent to the emulsification process is more typical.

After making a double emulsion, we can typically use methods of size fractionation such as centrifugation, ultracentrifugation, outer-droplet size-dependent depletion attractions, etc. to separate smaller outer droplets from larger ones according to some embodiments of the current invention. This may also potentially be used to separate out inner droplet volumes since the buoyancy of a droplet depends on its density, which is determined both by inner and outer droplet volumes.

The "boundary surface region" referred to herein includes the following. Practitioners in this art typically say that there is a "film" of the primary dispersed phase (i.e. oil) between the secondary dispersed phase (i.e. inner droplet of water) and the continuous phase (i.e. water solution). In a stable double emulsion, there is a disjoining pressure of this film that can resist thermal driving stresses, chemical driving stresses, and mild external agitation (e.g. physical shear stresses) and therefore the film is called "stable". Stability of the film is equivalent to the resistance to coalescence of the two oil-water interfaces that have mean curvatures of opposite signs (by commonly accepted conventions). Stability of the outer droplets from coarsening through coalescence is also generally desirable for having a useful product that remains shelf-stable. In this case, there is also at least a short-range repulsion that creates a repulsive disjoining pressure in the water film of continuous phase that separates the oil-water interfaces of two outer droplets that may closely approach.

Also, other types of materials can be used as stabilizers or surface modifiers, according to additional embodiments of the current invention, which could potentially be incorporated into the block copolymers that stabilize interfaces of double and multiple emulsions. Some potential copolymers include: lipo-polypeptides, glyco-polypeptides, and polynucleicacid-polypeptides (i.e. polypeptide-polynucleotide copolymers). For instance, a charged oligonucleotide or short polynucleotide (e.g. single-stranded DNA, double-stranded DNA, RNA, etc) could be substituted for the hydrophilic block and attached to a racemic hydrophobic block (e.g. rac-L) to confer the desired solubility and interfacial stability properties.

Another embodiment can include PEG-modified block copolymers: poly-(ethylene glycol)-poly-(peptide) specifically for use in making double emulsions and for decorating the surfaces of stable double emulsions (even if such PEGylated molecules might not create much additional interfacial stability). PEG and PEG derivatives are known to provide good resistant coatings for drug delivery vehicles, so it is anticipated that PEG-modified double emulsions could remain longer in circulation in the bloodstream.

It can be reasonably expected that the release of cargo, such as drug molecules, contained in double emulsions and double nanoemulsions can be triggered by a change in the pH, ionic strength, temperature, chemical environment, or a combination thereof. Such a change could affect the conformation, density, and interactions between copolypeptides that reside at oil-water interfaces, thereby altering the stability and creating conditions suitable for release. Likewise, because of their liquid nature, it can be expected that, according to some embodiments of the current invention, double emulsions can exhibit excellent clearance properties when introduced into an organism, including humans. This clearance property refers to mechanisms by which the organism can clear (i.e. digest, excrete, or otherwise get rid of) the droplet materials and associated stabilizing materials.

It can be reasonably expected that the following natural amino acids can be polymerized to become a portion of the molecular composition of the copolymer that stabilizes droplet structures, including but not limited to single droplet, double droplet, and multiple droplet structures. This stabilization would encompass nanoscale and larger droplet structures. These amino acids may come in a variety of forms, including but not limited to chiral, enantiomeric, and other molecular specifications, such as H-, L-, Z-D-, LD-, and rac-forms. The categorization as 'natural' is somewhat arbitrary, but a good guide for 'natural' amino acids can be deduced from the lists of products in the catalogs of large biochemical and chemical suppliers such as Sigma-Aldrich®. For instance, in their catalog, a wide variety of synthetic precursors are available for the following amino acids: Alanine, Arginine, Asparagine, Aspartic Acid, Cysteine/Cystine, Glutamic Acid, Glutamine, Glycine, Histidine, Isoleucine, Leucine, Lysine, Methionine, Phenylalanine, Proline, Serine, Threonine, Tryptophan, Tyrosine, Valine.

Although many of the examples described above demonstrate that using fully racemic amino-acids for the hydrophobic block in copolypeptides can promote the formation and stabilization of double emulsion structures, general aspects of this invention are not limited to only these examples. For example, it is possible to design and synthesize copolypeptides having hydrophobic blocks that contain a portion of non-racemic amino acids (i.e. either subsections of several D-amino acids in a row and/or subsections of several L-amino acids in a row within a hydrophobic block that contains some racemic nature) and that these copolypeptides could still confer a desirable property of promoting the formation and stabilization of double emulsions according to some embodiments of the current invention. Likewise, although we have shown examples that using non-racemic amino acids in the hydrophobic block in copolypeptides can tend to promote the formation and stabilization of single emulsions, it is possible to design and synthesize copolypeptides having hydrophobic blocks that contain a portion of racemic amino acids and that these copolypeptides could still confer a desirable property of promoting the formation and stabilization of single emulsions according to some embodiments of the current invention.

Other natural amino-acid-related structures can be polymerized to form a portion of the molecular composition of the copolymer that stabilizes double emulsions and double nanoemulsion structures. These include the following: Amino Alcohols, Amino Aldehydes, Amino Lactones, and n-Methyl Amino Acids.

Examples of unnatural amino acids and amino acid derivatives that can be part of the copolymer that stabilizes single, double, and multiple emulsions are: Alanine Derivatives, Alicyclic Amino Acids, Arginine Derivatives, Aromatic Amino Acids, Asparagine Derivatives, Aspartic Acid Derivatives, Beta-Amino Acids, Cysteine Derivatives, DAB (2,4-Diaminobutyric Acid), DAP (2,3-Diaminopropionic Acid), Glutamic Acid Derivatives, Glutamine Derivatives, Glycine Derivatives, Histidine Derivatives, Homo-Amino Acids, Isoleucine Derivatives, Leucine Derivatives, Linear Core Amino Acids, Lysine Derivatives, n-Methyl Amino Acids, Norleucine, Norvaline, Ornithine, Penicillamine, Phenylalanine Derivatives, Phenylglycine Derivatives, Proline Derivatives, Pyroglutamine Derivatives, Serine Derivatives, Threonine Derivatives, Tryptophan Derivatives, Tyrosine Derivatives, Valine Derivatives, as well as more than 100 'Other' derivative types of molecular compositions and structures listed in common catalogues of biochemical and chemical suppliers. For instance, there are more than a thousand types of unnatural amino acid derivatives listed as products of Sigma-Aldrich® in August, 2008. This number is likely to grow and will provide alternative other molecular structures that can be incorporated into copolypeptides used to stabilize emulsions, double emulsions, and multiple emulsions. Another source of potential molecular constituents that could be used to fabricate complex amphiphilic copolymers suitable for stabilizing single emulsions or double emulsions is BACHEM Americas Inc.'s 2008 "Building Blocks" and "Peptides and Biochemicals" catalogs (www.bachem.com), which describes many kinds of amino acid derivatives, special amino acids, resin-linked amino acids, and other linkers and reagents.

The copolymers that stabilize droplets can have molecular compositions and structures that include reactive groups (e.g. polymerizable groups, pH-sensitive groups, photo-reactive groups, and photo-polymerizable groups) which can be activated through chemical or physical changes to provide linking and/or coupling functionality between copolymer molecules on the same interface, copolymer molecules on adjacent inner and outer interfaces within the same double or multiple emulsion structure, between copolymer molecules on the interfaces of adjacent inner droplets, and between copolymer molecules on the interfaces of adjacent outer droplets.

The copolymers that stabilize droplets structures can have enzymatic and catalytic functionality. These include the following: Enzymes, Analytical Enzymes, Cofactors, Collagenases, Enzyme Inhibitors, Enzyme-Mediated Synthesis, Stabilizers, Enzyme Substrates, Lectins, Molecular Biology Enzymes, Kinases, Phosphatases, and Proteolytic Enzymes and Substrates. Other desirable functional molecular components of the copolymers can also be chosen and incorporated into copolymers, such as amine protectors, guanidine protectors, and guanidinylation.

Useful synthetic structures that can be polymerized to form a portion of the molecular composition of the copolymer stabilizes droplet structures, including but not limited to single droplet, double droplet, and multiple droplet structures, whether microscale or nanoscale droplet structures. These synthetic structures include, but are not limited to, the following: Poly-(ethylene glycol) (PEG), Functionalized Oligoethylene Glycols, Monofunctional PEGs, Homobifunctional PEGs, Heterobifunctional PEGs, PEGylated oligonucleotides, and PEGylated peptides.

In general, synthetic derivative molecules that mimic at least some aspects of the composition, structure, and function can be reasonably anticipated to provide stabilization to double emulsions similar to what we describe herein. Therefore, it can be reasonably anticipated that new unnatural amino-acid-like molecules developed in the future could also be used to stabilize double and multiple emulsion structures.

TABLE 1

Block copolypeptide surfactants used to prepare emulsions.

| Block Copolypeptide | $M_n \times (10^{-3})$* | Droplet Diameter (nm) | Inner/Outer Diameter Ratio | CAC (M) | Water Solubility Limit (mM) | Interfacial Tension (dyne/cm)† |
|---|---|---|---|---|---|---|
| $K_{20}(rac-L)_{10}$ | 5.5 | 380 | 0.52 | $1.5 \times 10^{-5}$ | N/A | N/A |
| $K_{40}(rac\ L)_5$ | 11.0 | 430 | 0.48 | $1.1 \times 10^{-4}$ | 11.5 | N/A |
| $K_{40}(rac-L)_{10}$ | 10.5 | 200 | 0.47 | $2.0 \times 10^{-5}$ | 8.5 | N/A |
| $K_{40}(rac-L)_{20}$ | 11.0 | 120 | 0.57 | $9.7 \times 10^{-7}$ | 3.0 | 25.3 |
| $K_{40}(rac-L)_{20}$** | 11.0 | 60 | 0.45 | N/A | N/A | N/A |
| $K_{40}(rac-L)_{30}$ | 11.1 | 60 | 0.52 | $3.6 \times 10^{-7}$ | 1.0 | N/A |
| $K_{60}(rac-L)_{20}$ | 16.2 | N/A | N/A | $3.6 \times 10^{-6}$ | 4.5 | N/A |
| $K_{100}(rac-L)_{10}$ | 27.1 | N/A | N/A | $3.6 \times 10^{-5}$ | N/A | N/A |
| $K_{60}(rac-A)_{20}$ | 16.3 | N/A | N/A | $4.1 \times 10^{-5}$ | N/A | N/A |
| $K_{60}(rac-V)_{20}$ | 15.8 | N/A | N/A | $4.9 \times 10^{-6}$ | N/A | N/A |
| $K_{60}L_{20}$# | 16.2 | 130 | N/A | $7.1 \times 10^{-7}$ | 2.5 | 33.4 |
| $R_{40}(rac-L)_{10}$ | 10.7 | 220 | 0.51 | $2.4 \times 10^{-5}$ | N/A | N/A |
| $E_{40}(rac-L)_{10}$ | 9.1 | 210 | 0.52 | $2.4 \times 10^{-5}$ | N/A | N/A |

*number average molecular masses determined using GPC-LS.
**This sample was fractionated from larger droplets by centrifugation followed by ultracentrifugation.
This sample formed a simple WO emulsion.
†Oil/water interfacial tension data of 10 cSt PDMS in contact with: 10 mM aqueous sodium dodecyl sulphate (SDS) solution = 12.4 dyne/cm; in contact with deionized water = 40.7 dyne/cm.
N/A = experiment not performed
All emulsions were prepared using a microfluidic homogenizer under the following conditions: number of passes N = 6, homogenizer inlet air pressure p = 130 psi, block copolypeptide concentration C = 1.0 mM, and oil volume fraction φ = 0.20. Diameters (of the outer droplets) and inner/outer diameter ratios were determined by averaging measurements of at least 50 droplets from CTEM images. Critical aggregation concentration (CAC) values were measured using pyrene fluorescence at 20° C. Water solubility limits were measured by diluting 15 mM stock solutions of each polypeptide until optically clear solutions were created. The block copolymers had negligible solubility in PDMS. Oil/water interfacial tension data were measured using the Du Nouy ring method using 10 cSt PDMS and block copolypeptide solutions (0.1 mM, pull rate = 0.01 mm/s, 25° C.).

We claim:

1. An emulsion, comprising:
a substantially continuous liquid medium; and
a plurality of droplet structures dispersed within said substantially continuous liquid medium,
wherein each droplet structure of said plurality of droplet structures comprises:
an outer droplet of a first liquid having an outer surface;
an inner droplet of a second liquid having an inner surface within said first droplet, said second liquid being immiscible in said first liquid, wherein said inner and outer droplets have a film of said first liquid in a surface boundary region therebetween;
an outer layer of block copolymers disposed on said outer surface of said outer droplet; and
an inner layer of block copolymers disposed on said inner surface of said inner droplets in proximity to said boundary surface region between said outer and said inner droplets,
wherein said block copolymers comprise a hydrophilic polymer block and a hydrophobic polymer block that act in combination to stabilize said droplet structure,
wherein said first liquid is immiscible in said substantially continuous liquid medium, and
wherein said hydrophilic polymer block is a polypeptide block comprising predominantly hydrophilic amino acids and said hydrophobic polymer block is a polypeptide block comprising predominantly hydrophobic amino acids.

2. An emulsion according to claim 1, wherein said droplet structure has a maximum dimension corresponding to an undeformed droplet diameter that is less than about 1000 nm and greater than about 10 nm.

3. An emulsion according to claim 1, wherein said droplet structure has a maximum dimension corresponding to an undeformed droplet diameter that is less than about 250 nm and greater than about 50 nm.

4. An emulsion according to claim 1, wherein block copolymers of said inner layer of block copolymers are of a substantially same molecular form as block coplolymers of said outer layer of block copolymers.

5. An emulsion according to claim 1, wherein said hydrophilic block has a molecular weight in the range from about 200 Da to about 3,000,000 Da and said hydrophobic block has a molecular weight in the range from about 200 Da to about 3,000,000 Da.

6. An emulsion according to claim 1, wherein a dimensionless ratio, defined by the average radius of said inner droplet divided by the average radius of said outer droplet, is less than about 0.9 and greater than about 0.05.

7. An emulsion according to claim 1, wherein said inner layer of block copolymers is a layer of di-block copolymers formed from polymerization of two distinguishably different monomer types and said outer layer of block copolymers is a layer of di-block copolymers formed from polymerization of two said monomer types.

8. An emulsion according to claim 1, wherein said hydrophilic polymer block is a polypeptide block comprising a plurality of types of hydrophilic amino acids and said hydrophobic polymer block is a polypeptide block comprising a plurality of types of hydrophobic amino acids.

9. An emulsion according to claim 1, wherein said hydrophilic amino acids are selected from the group of hydrophilic amino acids consisting of L-argenine, L-asparagine, L-aspartic acid, L-cysteine, L-glutamic acid, L-glutamine, L-histidine, L-lysine, L-serine, L-threonine, L-tyrosine, D-argenine, D-asparagine, D-aspartic acid, D-cysteine, D-glutamic acid, D-glutamine, D-histidine, D-lysine, D-serine, D-threonine, D-tyrosine, DL-argenine, DL-asparagine, DL-aspartic acid, DL-cysteine, DL-glutamic acid, DL-glutamine, DL-histidine, DL-lysine, DL-serine, DL-threonine, DL-tyrosine, and any combination thereof.

10. An emulsion according to claim 1, wherein said hydrophobic amino acids are selected from the group of hydrophobic amino acids consisting of racemic-alanine, racemic-glycine, racemic-isoleucine, racemic-leucine, racemic-methionine, racemic-phenylanaline, racemic-proline, racemic-tryptophan, racemic-valine, and any combination thereof.

11. An emulsion according to claim 10, wherein said hydrophobic amino acids are selected from the group of hydrophobic amino acids consisting of racemic-alanine, racemic-glycine, racemic-isoleucine, racemic-leucine, racemic-methionine, racemic-phenylanaline, racemic-proline, racemic-tryptophan, racemic-valine and any combination thereof.

12. An emulsion according to claim 1, wherein said hydrophilic amino acids and said hydrophobic amino acids are selected from the group of amino acids consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, and any combination thereof.

13. An emulsion according to claim 1, wherein said hydrophilic amino acids are L-lysine and said hydrophobic amino acids are racemic-leucine.

14. An emulsion according to claim 1, wherein said block copolymers are bock copolypeptides having a structure satisfying the formula $K_x rL_y$, K representing L-lysine and rL representing racemic-leucine, wherein x is an integer in the range 10 to 200 and y is an integer in the range 3 to 30.

15. An emulsion according to claim 1, wherein said second liquid of said inner droplet is hydrophilic and further comprises, at least one of blended or dispersed therein, at least one of single-stranded DNA, double-stranded DNA, RNAs, oligonucleotides, peptides, proteins, salts, viruses, vitamins, serums, lysates, ATP, GTP, molecular motors, hydrophilic drug molecules, cells, vesicles, nanodroplets, nanoparticles, fullerenes, single-walled carbon nanotubes, multi-walled carbon nanotubes, cytoplasm, ribosomes, enzymes, glucose, hemoglobin, golgi, dendrimers, surfactants, lipids, albumin, anions, cations, buffers, sugars, saccharides, quantum dots, clay nanoparticles, metal nanoclusters, metal nanoparticles, magnetically responsive iron oxide nanoparticles, organic nanospheres, organic nanoparticles, inorganic nanospheres, inorganic nanoparticles, fluorescent dyes, transfection agents, antiseptic materials, antimicrobial materials, materials that absorb electromagnetic radiation, isotopically specific materials, molecules containing radioactive isotopes, imaging-contrast enhancement agents, agents that disrupt cellular functions, agents that enhance cellular functions, agents that disrupt cellular substructures, agents that modify cellular substructures, agents that affect cellular metabolic pathways, agents that trigger cellular apoptosis and combinations thereof.

16. An emulsion according to claim 1, wherein said first liquid of said outer droplet is hydrophobic and further comprises, at least one of blended or dispersed therein, at least one of fats, lipids, waxes, natural oils, synthetic oils, silicone oils, volatile oils essential oils, fragrances, cholesterol, steroids, hydrophobic drug molecules, polymers, block copolymers, poly-acids, poly-bases, polypeptides, block copolypeptides, micelles, quantum dots, nanoparticles, nanoclusters, carbon nanotubes, fullerenes, ferrofluids, thermotropic liquid crystals, lyotropic liquid crystals, fluorinated liquids, brominated liquids, plant-derived materials, animal-derived materials, bacterially-derived materials, and combinations thereof.

17. An emulsion according to claim 16, wherein said first liquid of said outer droplet is hydrophobic and further comprises, at least one of blended or dispersed therein, at least one of fats, lipids, waxes, natural oils, synthetic oils, silicone oils, volatile oils, essential oils, fragrances, cholesterol, steroids, hydrophobic drug molecules, polymers, block copolymers, polypeptides, block copolypeptides, poly-acids, poly-bases, micelles, quantum dots, nanoparticles, nanoclusters, carbon nanotubes, fullerenes, ferrofluids, thermotropic liquid crystals, lyotropic liquid crystals, fluorinated liquids, brominated liquids, plant-derived materials, animal-derived materials, bacterially-derived materials, and combinations thereof.

18. A droplet structure, comprising:
an outer droplet of a first liquid having an outer surface;
an inner droplet of a second liquid having an inner surface within said first droplet, said second liquid being immiscible in said first liquid, wherein said inner and outer droplets have a film of said first liquid in a boundary surface region therebetween;
an outer layer of block copolymers disposed on said outer surface of said outer droplet; and
an inner layer of block copolymers disposed on said inner surface of said inner droplet,
wherein said block copolymers comprise a hydrophilic polymer block and a hydrophobic polymer block that act in combination to stabilize said outer surface of said outer droplet from coalescing with said inner surface of said inner droplet and to stabilize said droplet structure from coalescing with other droplet structures, and
wherein said hydrophilic polymer block is a polypeptide block comprising predominantly hydrophilic amino acids and said hydrophobic polymer block is a polypeptide block comprising predominantly hydrophobic amino acids.

19. A droplet structure according to claim 18, wherein said droplet structure has a maximum dimension given by an undeformed droplet diameter that is less than about 1000 nm and greater than about 10 nm.

20. A droplet structure according to claim 18, wherein said droplet structure has a maximum dimension given by an undeformed droplet diameter that is less than about 250 nm and greater than about 50 nm.

21. A droplet structure according to claim 18, wherein block copolymers of said inner layer of block copolymers are of a substantially same molecular form as block coplolymers of said outer layer of block copolymers.

22. A droplet structure according to claim 18, wherein said hydrophilic block has a molecular weight in the range from about 200 Da to about 3,000,000 Da and said hydrophobic block has a molecular weight in the range from about 200 Da to about 3,000,000 Da.

23. A droplet structure according to claim 18, wherein a ratio given by a radius of said outer droplet divided by a radius of said inner droplet is less than about 0.9 and greater than about 0.05.

24. A droplet structure according to claim 18, wherein said inner layer of block copolymers is a layer of di-block copolymers formed from polymerization of two distinguishably different monomer types and said outer layer of block copolymers is a layer of di-block copolymers formed from polymerization of two said monomer types.

25. A droplet structure according to claim 18, wherein at least one of said polypeptide blocks comprises a surface moiety to provide surface functionalization.

26. A droplet structure according to claim 18, wherein said hydrophilic polymer block is a polypeptide block comprising predominantly a plurality of types of hydrophilic amino acids and said hydrophobic polymer block is a polypeptide block comprising predominantly a plurality of types of hydrophobic amino acids.

27. A droplet structure according to claim 18, wherein said hydrophilic amino acids are selected from the group of hydrophilic amino acids consisting of L-argenine, L-asparagine, L-aspartic acid, L-cysteine, L-glutamic acid, L-glutamine, L-histidine, L-lysine, L-serine, L-threonine, L-tyrosine, D-argenine, D-asparagine, D-aspartic acid, D-cysteine, D-glutamic acid, D-glutamine, D-histidine, D-lysine, D-serine, D-threonine, D-tyrosine, DL-argenine, DL-asparagine, DL-aspartic acid, DL-cysteine, DL-glutamic acid, DL-glutamine, DL-histidine, DL-lysine, DL-serine, DL-threonine, DL-tyrosine, and any combination thereof.

28. A droplet structure according to claim 18, wherein said hydrophobic amino acids are selected from the group of hydrophobic amino acids consisting of racemic-alanine, racemic-glycine, racemic-isoleucine, racemic-leucine, racemic-methionine, racemic-phenylanaline, racemic-proline, racemic-tryptophan, racemic-valine, and any combination thereof.

29. A droplet structure according to claim 27, wherein said hydrophobic amino acids are selected from the group of hydrophobic amino acids consisting of racemic-alanine, racemic-glycine, racemic-isoleucine, racemic-leucine, racemic-methionine, racemic-phenylanaline, racemic-proline, racemic-tryptophan, racemic-valine, and any combination thereof.

30. A droplet structure according to claim 18, wherein said hydrophilic amino acids and said hydrophobic amino acids are selected from the group of amino acids consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, and any combination thereof.

31. A droplet structure according to claim 18, wherein said hydrophilic amino acids are L-lysine and said hydrophobic amino acids are racemic-leucine.

32. A droplet structure according to claim 18, wherein said block copolymers are bock copolypeptides having a structure satisfying the formula $K_xrL_y$, K representing L-lysine and rL representing racemic-leucine, wherein x is an integer in the range from about 10 to about 200 and y is an integer in the range from about 3 to about 30.

33. A droplet structure according to claim 18, wherein said second liquid of said inner droplet is hydrophilic and further comprises, at least one of blended or dispersed therein, at least one of single-stranded DNA, double-stranded DNA, RNAs, oligonucleotides, peptides, proteins, salts, viruses, vitamins, serums, lysates, ATP, GTP, molecular motors, hydrophilic drug molecules, cells, vesicles, nanodroplets, nanoparticles, fullerenes, single-walled carbon nanotubes, multi-walled carbon nanotubes, cytoplasm, ribosomes, enzymes, glucose, hemoglobin, golgi, dendrimers, surfactants, lipids, albumins, anions, cations, buffers, sugars, saccharides, quantum dots, clay nanoparticles, metal nanoclusters, metal nanoparticles, magnetically responsive iron oxide nanoparticles, organic nanospheres, organic nanoparticles, inorganic nanospheres, inorganic nanoparticles, fluorescent dyes, transfection agents, antiseptic materials, antimicrobial materials, materials that absorb electromagnetic radiation, isotopically specific materials, molecules containing radioactive isotopes, imaging-contrast enhancement agents, agents that enhance magnetic resonance imaging, agents that enhance x-ray imaging, agents that enhance neutron imaging, agents that enhance positron-emission tomography, agents that enhance light scattering, agents that disrupt cellular functions, agents that enhance cellular functions, agents that disrupt cellular substructures, agents that modify cellular substructures, agents that affect cellular metabolic pathways, agents that trigger cellular apoptosis and combinations thereof.

34. A droplet structure according to claim 18, wherein said first liquid of said outer droplet is hydrophobic and further comprises, at least one of blended or dispersed therein, at least one of fats, lipids, waxes, natural oils, synthetic oils, silicone oils, volatile oils, essential oils, fragrances, cholesterol, steroids, hydrophobic drug molecules, polymers, block polymers, poly-acids, poly-bases, polypeptides, block polypeptides, micelles, quantum dots, nanoparticles, nanoclusters, carbon nanotubes, fullerenes, ferrofluids, thermotropic liquid crystals, lyotropic liquid crystals, fluorinated liquids, brominated liquids, plant-derived materials, animal-derived materials, bacterially-derived materials, and combinations thereof.

35. A droplet structure according to claim 33, wherein said first liquid of said outer droplet is hydrophobic and further comprises, at least one of blended or dispersed therein, at least one of fats, lipids, waxes, natural oils, synthetic oils, synthetic oils, volatile oils, essential oils, fragrances, cholesterol, steroids, hydrophobic drug molecules, polymers, block polymers, poly-acids, poly-bases, polypeptides, block polypeptides, micelles, quantum dots, nanoparticles, nanoclusters, carbon nanotubes, fullerenes, ferrofluids, thermotropic liquid crystals, lyotropic liquid crystals, fluorinated liquids, brominated liquids, plant-derived materials, animal-derived materials, bacterially-derived materials, and combinations thereof.

36. A nano-droplet structure, comprising:
an outer droplet of a first liquid having an outer surface;
an inner droplet of a second liquid having an inner surface arranged within said first droplet, said second liquid being immiscible in said first liquid, wherein said inner and outer droplets have a film of said first liquid in a boundary surface region therebetween;
an outer layer of block copolypeptides disposed on said outer surface of said outer droplet; and
an inner layer of block copolypeptides disposed on said inner surface proximate to said boundary surface region between said outer and said inner droplets,
wherein said block copolypeptides have a structure satisfying the formula $K_xrL_y$, K representing L-lysine and rL representing racemic-leucine,
wherein x is an integer in the range from about 10 to about 200 and y is an integer in the range from about 3 to about 30, and
wherein said nano-droplet structure has a maximum dimension given by an undeformed outer droplet diameter that is less than about 300 nm and greater than about 10 nm.

37. A nano-droplet structure according to claim 36, wherein said second liquid of said inner droplet is hydrophilic and further comprises, at least one of blended or dispersed therein, at least one of single-stranded DNA, double-stranded DNA, RNAs, oligonucleotides, peptides, proteins, salts, viruses, vitamins, serums, lysates, ATP, GTP, molecular motors, hydrophilic drug molecules, cells, vesicles, nanodroplets, nanoparticles, fullerenes, single-walled carbon nanotubes, multi-walled carbon nanotubes, cytoplasm, ribosomes, enzymes, glucose, hemoglobin, golgi, dendrimers, surfactants, lipids, albumins, anions, cations, buffers, sugars, saccharides, quantum dots, clay nanoparticles, metal nanoclusters, metal nanoparticles, magnetically responsive iron oxide nanoparticles, organic nanospheres, organic nanoparticles, inorganic nanospheres, inorganic nanoparticles, fluorescent dyes, transfection agents, antiseptic materials, antimicrobial materials, materials that absorb electromagnetic radiation, isotopically specific materials, molecules containing radioactive isotopes, imaging-contrast enhancement agents, agents that enhance magnetic resonance imaging, agents that enhance x-ray imaging, agents that enhance neutron imaging, agents that enhance positron-emission tomography, agents that enhance light scattering, agents that disrupt cellular functions, agents that enhance cellular functions, agents that disrupt cellular substructures, agents that modify cellular substructures, agents that affect cellular metabolic pathways, agents that trigger cellular apoptosis and combinations thereof.

38. A nano-droplet structure according to claim 36, wherein said first liquid of said outer droplet is hydrophobic and further comprises, at least one of blended or dispersed therein, at least one of fats, lipids, waxes, natural oils, synthetic oils, silicone oils, volatile oils, essential oils, fragrances, cholesterol, steroids, hydrophobic drug molecules, polymers, block copolymers, polypeptides, block polypeptides, poly-acids, poly-bases, micelles, quantum dots, nanoparticles, nanoclusters, carbon nanotubes, fullerenes, ferrofluids, thermotropic liquid crystals, lyotropic liquid crystals, fluorinated liquids, brominated liquids, plant-derived materials, animal-derived materials, bacterially-derived materials, and combinations thereof.

39. A droplet structure according to claim 37, wherein said first liquid of said outer droplet is hydrophobic and further comprises, at least one of blended or dispersed therein, at least one of fats, lipids, waxes, natural oils, synthetic oils, silicone oils, volatile oils, essential oils, fragrances, cholesterol, steroids, hydrophobic drug molecules, polymers, block polymers, polypeptides, block polypeptides, poly-acids, poly-bases, micelles, quantum dots, nanoparticles, nanoclusters, carbon nanotubes, fullerenes, ferrofluids, thermotropic liquid crystals, lyotropic liquid crystals, fluorinated liquids, brominated liquids, plant-derived materials, animal-derived materials, bacterially-derived materials, and combinations thereof.

40. An emulsion, comprising:
a liquid medium;
a plurality of nano-droplets dispersed within said liquid medium; and
first block copolymers adsorbed onto a surface of said plurality of nano-droplets and second block copolymers adsorbed onto a surface of said inner droplets,
wherein each of said plurality of nano-droplets comprises an inner droplet of a first liquid surrounded by a second liquid, said first liquid being immiscible in said second liquid and said second liquid being immiscible in said liquid medium,
wherein said plurality of nano-droplets have an ensemble average undeformed outer droplet diameter of at least about 10 nm and less than about 300 nm,
wherein said first and second block copolymers each comprises a hydrophilic polymer block and a hydrophobic polymer block that act in combination to stabilize at least one of said plurality of nano-droplets or said inner droplets,
wherein said hydrophilic polymer block is a polypeptide block comprising predominantly hydrophilic amino acids and said hydrophobic polymer block is a polypeptide block comprising predominantly hydrophobic amino acids.

41. An emulsion according to claim 40, wherein said liquid medium is a same material as said first liquid.

42. An emulsion according to claim 40, further comprising block copolymers adsorbed onto at least one of a surface of said plurality of nano-droplets and a surface of said inner droplets.

43. An emulsion according to claim 42, wherein said block copolymers each comprises a hydrophilic polymer block and a hydrophobic polymer block that act in combination to stabilize at least one of said plurality of nano-droplets or said inner droplets.

44. An emulsion according to claim 40, wherein said first and second block copolymers are of a substantially same molecular structure.

45. An emulsion, comprising:
a substantially continuous liquid medium; and
a plurality of droplet structures dispersed within said substantially continuous liquid medium,
wherein each droplet structure of said plurality of droplet structures comprises:
a droplet of a liquid having an outer surface; and
a layer of block copolymers disposed on said outer surface of said droplet,
wherein said block copolymers comprise a hydrophilic polymer block and a hydrophobic polymer block that act in combination to stabilize said droplet structure, and
wherein said liquid of said plurality of droplet structures is immiscible in said substantially continuous liquid medium, and
wherein said hydrophilic polymer block is a polypeptide block comprising predominantly hydrophilic amino acids and said hydrophobic polymer block is a polypeptide block comprising predominantly hydrophobic amino acids.

46. An emulsion according to claim 45, wherein said hydrophilic polymer block is a polypeptide block comprising a plurality of types of predominantly hydrophilic amino acids and said hydrophobic polymer block is a polypeptide block comprising a plurality of types of predominantly hydrophobic amino acids.

47. An emulsion according to claim 45, wherein said hydrophilic amino acids and said hydrophobic amino acids are selected from the group of amino acids consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, and any combination thereof.

48. An emulsion according to claim 47, wherein said each droplet structure has a maximum dimension corresponding to an undeformed droplet diameter that is less than about 300 nm and greater than about 10 nm.

49. A method of producing an emulsion, comprising:
at least one of adding a surfactant to at least one of a first liquid and a second liquid, or adding surfactant precursors to at least one of said first liquid and said second liquid;
emulsifying said first liquid in said second liquid to form a plurality of droplets of said first liquid immersed in said second liquid to provide a simple emulsion, said first liquid being immiscible in said second liquid;

adding at least one of said surfactant or said surfactant precursors to a third liquid;

emulsifying said simple emulsion in said third liquid to form a plurality of droplets of said simple emulsion to provide a double emulsion, said second liquid being immiscible in said third liquid; and adding a selected quantity of block copolymers to at least one of said first, second or third liquids prior to the first or second said emulsifying, wherein said plurality of droplets of said double emulsion each comprises at least one droplet of said first liquid therein, and wherein said block copolymers comprise a hydrophilic polymer block and a hydrophobic polymer block that act in combination to stabilize said droplets, and wherein said hydrophilic polymer block is a polypeptide block comprising predominantly hydrophilic amino acids and said hydrophobic polymer block is a polypeptide block comprising predominantly hydrophobic amino acids.

50. An emulsion produced according to the method of claim 49.

* * * * *